United States Patent [19]

Sanguinetti et al.

[11] Patent Number: 5,597,818
[45] Date of Patent: *Jan. 28, 1997

[54] METHODS OF TREATING CARDIAC ARRHYTHMIA

[75] Inventors: Michael C. Sanguinetti, Park City, Utah; Joseph J. Salata, Newtown; Joseph J. Lynch, Jr., Lansdale, both of Pa.

[73] Assignee: Merck & Co., Inc., Rahway, N.J.

[*] Notice: The term of this patent shall not extend beyond the expiration date of Pat. No. 5,428,031.

[21] Appl. No.: 407,337

[22] Filed: Mar. 20, 1995

Related U.S. Application Data

[63] Continuation of Ser. No. 156,184, Nov. 22, 1993, Pat. No. 5,428,031, which is a continuation-in-part of Ser. No. 18,912, Feb. 17, 1993, abandoned, which is a continuation of Ser. No. 802,000, Dec. 3, 1991, abandoned.

[51] Int. Cl.$^6$ ............................................. A61K 31/55
[52] U.S. Cl. ........................................ 514/221; 514/821
[58] Field of Search .................................. 514/221, 821

[56] References Cited

U.S. PATENT DOCUMENTS

| | | | |
|---|---|---|---|
| 4,470,988 | 9/1984 | Watthey | 424/263 |
| 4,473,575 | 9/1984 | Watthey | 424/263 |
| 4,507,313 | 3/1985 | Braestrup et al. | 514/220 |
| 4,600,534 | 7/1986 | Bach et al. | 260/239.3 B |
| 4,775,671 | 10/1988 | Hunkeler et al. | 514/220 |
| 4,820,834 | 4/1989 | Evans et al. | 540/504 |
| 4,847,248 | 7/1989 | Freidinger et al. | 514/214 |
| 5,044,741 | 4/1991 | Evans et al. | 514/221 |
| 5,166,151 | 11/1992 | Freidinger et al. | 514/215 |
| 5,428,031 | 6/1995 | Sanguinetti et al. | 514/221 |

FOREIGN PATENT DOCUMENTS

| | | |
|---|---|---|
| 1190708 | 7/1985 | Canada . |
| 0538945A1 | 4/1993 | European Pat. Off. . |
| 0107095 | 5/1994 | European Pat. Off. . |
| 93/15068 | 1/1993 | Japan . |

OTHER PUBLICATIONS

J. Gen. Physiol., vol. 96, Jul. 1990, pp. 195–215, by M. C. Sanguinetti, et al.

J. Cardiovascular Pharmacology, vol. 20 (Suppl. 2), pp. S17–S22 (1992), by L. M. Hondeghem.

*Primary Examiner*—Kimberly Jordan
*Attorney, Agent, or Firm*—Francis P. Bigley; Mark R. Daniel

[57] ABSTRACT

Benzodiazepine analogs have been found to be useful in treating cardiac abnormalities.

1 Claim, No Drawings

METHODS OF TREATING CARDIAC ARRHYTHMIA

CROSS REFERENCE

This is a continuation of application Ser. No. 08/156,184 filed Nov. 22, 1993, now U.S. Pat. No. 5,428,031, which is a continuation in part of U.S. patent application Ser. No. 08/018,912 which was filed on Feb. 17, 1993, now abandoned, which is a continuation of U.S. patent application Ser. No. 07/802,000 which was filed on Dec. 3, 1991, now abandoned.

BACKGROUND OF THE INVENTION

Cardiac arrhythmias often occur as complications to cardiac diseases such as myocardial infarction and heart failure. In serious cases, arrhythmias give rise to ventricular fibrillation and can cause sudden death.

Although various antiarrythmic agents are now available on the market, those having both satisfactory efficacy and a high margin of safety have not been obtained. For example, antiarrythmic agents of Class I according to the classification scheme of Vaughan-Williams ("Classification of anti-arrythmic drugs", In: Cardiac Arrhythmias, edited by: E. Sandoe, E. Flensted-Jensen, K. Olesen; Sweden, Astra, Sodertalje, pp 449–472, 1981) which cause a selective inhibition of the maximum velocity of the upstroke of the action potential (Vmax) are inadequate for preventing ventricular fibrillation. In addition, they have problems regarding safety, namely, they cause a depression of myocardial contractility and have a tendency to induce arrhythmias due to an inhibition of impulse conduction. Beta-adrenoceptor blockers and calcium antagonists which belong to Class II and IV, respectively, have a defect in that their effects are either limited to a certain type of arrhythmia or are contraindicated because of their cardiac depressant properties in certain patients with cardiovascular disease. Their safety, however, is higher than that of the antiarrhythmic agents of Class I.

Antiarrhythmic agents of Class III are drugs that cause a selective prolongation of the duration of the action potential without a significant depression of the Vmax. Available drugs in this class are limited in number. Examples such as sotalol and amiodarone have been shown to possess interesting Class III properties (Singh B. N., Vaughan Williams E. M. "A third class of anti-arrhythmic action: effects on atrial and ventricular intracellular potentials and other pharmacological actions on cardiac muscle, of MJ 1999 and AH 3747" Br. J. Pharmacol 39:675–689, 1970; and Singh B. N., Vaughan Williams E. M, "The effect of amiodarone, a new anti-anginal drug, on cardiac muscle", Br J. Pharmacol 39:657–667 1970.), but these are not selective Class III agents. Sotalol also possesses Class II effects which may cause cardiac depression and is contraindicated in certain susceptible patients. Amiodarone, also is not a selective Class III antiarrhythmic agent because it possesses multiple electrophysiological actions and is severely limited by side effects (Nademanee, K. "The Amiodarone Odessey", J. Am. Coil. Cardiol. 20:1063–1065, 1992.) Drugs of this class are expected to be effective in preventing ventricular fibrillation. Selective class III agents, by definition, are not considered to cause myocardial depression or an induction of arrhythmias due to inhibition of conduction of the action potential as seen with Class I antiarrhythmic agents.

Class III agents increase myocardial refractoriness via a prolongation of cardiac action potential duration. Theoretically, prolongation of the cardiac action potential can be achieved by enhancing inward currents (i.e. $Na^+$ or $Ca^{2+}$ currents; hereinafter $I_{Na}$ and $I_{Ca}$ respectively) or by reducing outward repolarizing potassium ($K^+$) currents. The delayed rectifier ($I_K$) $K^+$ current is the main outward current involved in the overall repolarization process during the action potential plateau, whereas the transient outward ($I_{to}$) and inward rectifier ($I_{K1}$)$K^+$ currents are responsible for the rapid initial and terminal phases of repolarization, respectively. Cellular electrophysiologic studies have demonstrated that $I_K$ consists of two pharmacologically and kinetically distinct $K^+$ current subtypes, $I_{Kr}$ (rapidly activating and deactivating) and $I_{Ks}$ (slowly activating and deactivating). Class III antiarrhythmic agents currently in development, including d-sotalol, dofetilide (UK68,798), almokalant (H234/09), E-4031 and methanesulfonamide-N-[1'-6-cyano-1,2,3,4-tetrahydro-2-(R)-naphthalenyl)-3,4-dihydro-4(R)-hydroxyspiro[2H-1-benzopyran-2,4'-piperidin]-6yl],(+)-,monochloride predominantly, if not exclusively, block $I_{Kr}$. Although, amiodarone is a blocker of $I_{Ks}$ (Balser J. R. Bennett, P. B., Hondeghem, L. M. and Roden, D. M. "Suppression of time-dependent outward current in guinea pig ventricular myocytes: Actions of quinidine and amiodarone. Circ. Res. 1991, 69: 519–529), it also blocks $Na^+$ and $Ca^{2+}$ currents, effects thyroid function, is as a nonspecific adrenergic blocker, and acts as an inhibitor of the enzyme phospholipase (Nademanee, K. "The Amiodarone Odessey". J. Am. Coll. Cardiol. 1992; 20:1063–1065). Therefore, its method of treating arrhythmia is uncertain.

Most Class III agents that are known to be in development predominantly block $I_{Kr}$. These agents have a potential liability in that they have an enhanced risk of proarrhythmia at slow heart rates. For example, torsades de points has been observed when these compounds are utilized (Roden, D. M. "Current Status of Class III Antiarrhythmic Drug Therapy", Am J. Cardiol, 72:44B–49B, 1993.). This exaggerated effect at slow heart rates has been termed "reverse frequency-dependency", and is in contrast to frequency-independent or frequency-dependent actions (Hondeghem, L. M. "Development of Class III Antiarrhythmic Agents". J. Cadiovasc. Cardiol. 20(Suppl. 2):S17–S22).

A number of antiarrhythmic agents have been reported in the literature, such as those disclosed in:

(1) EP-A-O 397,121-A,
(2) EP-A-O 300,908-A,
(3) EP-A-O 307, 1 21,
(4) U.S. Pat. No. 4,629,739,
(5) U.S. Pat. No. 4,544,654,
(6) U.S. Pat. No. 4,788,196,
(7) EP application No. 88302597.5,
(8) EP application No. 88392598.3,
(9) EP application No. 88302270.9,
(10) EP application No. 88302600.7,
(11) EP application No. 88302599.1,
(12) EP application No. 88300962.3,
(13) EP-A-O 235,752,
(14) DE No. 3633977-A1,
(15) U.S. Pat. No. 4,804,662,
(16) U.S. Pat. No. 4,797,401,
(17) U.S. Pat. No. 4,806,555,
(18) U.S. Pat. No. 4,806,536,

(19) U.S. Pat. No. 5,032,598,

(20) U.S. Pat. No. 5,032,604. Despite considerable progress there is still a need for new methods to treat cardiac arrhythmia. In an effort to overcome the side effects inherent in currently available antiarrhythmic agents, compounds that treat arrhythmia through blockade of $I_{Ks}$ are presented.

OBJECTS OF THE INVENTION

It is, accordingly, an object of the present invention to provide methods of treating cardiac arrhythmia with compounds not previously known to have activity for this condition. Another object is to provide new methods for treating cardiac arrhythmia. A further object is to provide pharmaceutical formulations and methods for their preparation for use in treating cardiac arrhythmia. These and other objects of the present invention will be apparent from the following description.

SUMMARY OF THE INVENTION

A method of treating cardiac arrhythmia in mammals comprising block of the slowly activating delayed rectifier potassium (K$^+$)current ($I_{Ks}$) is presented.

Among the compounds which exemplify this method of treatment are the 1,4-benzodiazepines or benzodiazepine derivatives that block the $I_{Ks}$ current and are therefore effective in the treatment of cardiac arrhythmia.

Additionally, it has been found that compounds, which at a concentration of 1 μM or less (IC$_{50}$), selectively block 50% of the IKs current measured in isolated myocytes and exhibit a selectivity ratio equal to or greater than 10 times the block of the $I_{Kr}$, $I_{K1}$ currents, result in treatment which prolongs the cardiac refractory period equally well or to a greater extent as heart rate increases, producing a frequency-independent or frequency-dependent treatment.

Benzodiazepine analogs of the general formula

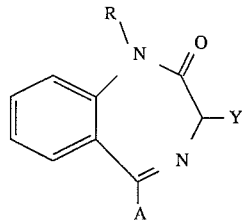

wherein A is a 6-membered saturated or unsaturated carbocyclic ring or a 6-membered heterocyclic ring containing N, or N and O, Y is —NH$_2$, NHSO$_2$R$^1$,

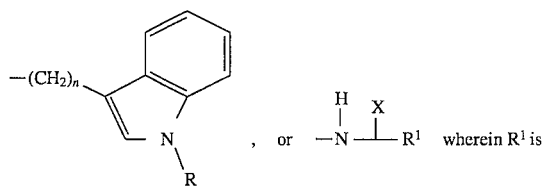

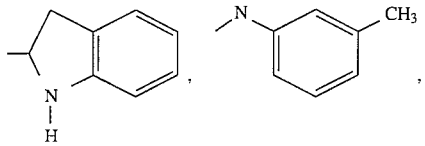

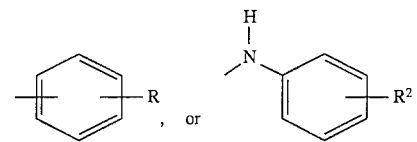

n is 0 or 1, X is O or —CH$_2$R, R$^2$ is R or —CONHSO$_2$R and R is straight or branched C$_{1-6}$ alkyl or C1–3alkylamine wherein the amino group is optionally mono- or di-substituted by C$_{1-3}$alkyl have been found to be useful in treating cardiac arrhythmia.

DETAILED DESCRIPTION

A method of treating cardiac arrhythmia in mammals comprising block of the slowly activating delayed rectifier potassium (K$^+$)current ($I_{Ks}$) is presented.

Among the compounds which exemplify this method of treatment are the 1,4-benzodiazepines or benzodiazepine derivatives that block the $I_{Ks}$ current and are therefore effective in the treatment of cardiac arrhythmia.

Additionally, it has been found that compounds, which at a concentration of 1 μM or less (IC$_{50}$), selectively block 50% of the IKs current measured in isolated myocytes and exhibit a selectivity ratio equal to or greater than 10 over block of the $I_{Kr}$, $I_{K1}$ currents, result in treatment which prolongs the cardiac refractory period equally well or to a greater extent as heart rate increases, producing a frequency-independent or frequency-dependent treatment.

Several of the compounds used according to the present invention are known per se as antagonists of gastrin and cholecystokinin (CCK). The invention includes racemic mixtures of these compounds, the separated R and S enantiomers, and preferably, the R enantiomer. Examples of suitable compounds according to the present invention are disclosed in U.S. Pat. No. 4,820,834, EP-A-0 434 360 and EP-A-0 434 369. Examples of some preferred compounds are listed below of this type:

1. 3(R)-(+)-1,3-dihydro-3-(2-indolecarbonylamino)-1-methyl-5-phenyl-2H-1,4-benzodiazepin-2-one.
2. 3(S)-(−)-1,3-dihydro-3-(2-indolecarbonylamino)-1-methyl-5-phenyl-2H-1,4-benzodiazepin-2-one.
3. N-(2,3-dihydro-1-methyl-2-oxo-5-phenyl-1H-1,4-benzodiazepin-3-yl)-N'-(3-methylphenyl)urea.
4. (R)-N-(2,3-dihydro-1-methyl-2-oxo-5-phenyl-1H-1,4-benzodiazepin-3-yl)-N'-(3-methylphenyl)urea.
5. N-[3(R,S)-5-cyclohexyl-2,3-dihydro-1-methyl-2-oxo-1H-1,4-benzodiazepin-3-yl]-N'-[3-(isopropylsulfonylaminocarbonyl)phenyl]urea, example 2 herein.
6. N,N-dimethyl-4-(3(R,S)-(((3-methylphenyl)amino)carbonyl)amino-1,3-dihydro-1 -(2-methylpropyl)-2-oxo-1,4-benzodiazepin-5-yl)phenylmethylamine.
7. (R)-3-amino-1,3-dihydro-1-methyl-5-phenyl-2H-1,4-benzodiazepin-2-one.
8. N-(2,3-dihydro-1-methyl-2-oxo-5-phenyl-1H-1,4-benzodiazepin-3-yl)-N'-(m-methylphenyl)urea.

9. (.±.)-N-(2,3-dihydro-1-methyl-2-oxo-5-(4-pyridinyl)-1H-1,4-benzodiazepin-3-yl-1H-indole-2carboxamide.

10. N-(2,3-dihydro-1-methyl-2-oxo-5-phenyl-1H-1,4-benzodiazepin-3-yl)-4-methylbenzenesulfonamide.

11. (R)-1-(2-(dimethylaminoethyl)-5-(2-fluorophenyl)-1,3-dihydro-3-((1-methyl-1H-indole-3-yl)methyl)-2H-benzodiazepin-2-one.

12. N-(2,3-dihydro-1-methyl-2-oxo-5-(4-morpholino)-1H-1,4-benzodiazepin-3-yl)-N'-3-methylphenylurea.

Additional benzodiazepines or benzodiazepine derivatives have also been found to block the $I_{Ks}$ current. Representative compounds capable of blocking this current are presented in the Example section below Certain compounds have been shown to exhibit selective block of the $I_{Ks}$ current. Examples of these compounds are:

a. (3RS)-N-(2,3-dihydro-1-methyl-2-oxo-5-Phenyl-1H-1,4-benzodiazepin-3-yl)-N'-(3-methylphenyl)-urea.

b. (3R)-N-(2,3-dihydro-1-methyl-2-oxo-5-phenyl-1H-1,4-benzodiazepin-3-yl)-N'-(3-methylphenyl)-urea.

c. E-(+)-N-[(3R )-2,3-dihydro-1-methyl-2-oxo-5-phenyl-1H-1,4-benzodiazepin- 3-yl)-N'-(3-methylphenyl)-urea.

d. (+)-N-[(3R )-2,3-dihydro-1-methyl-2-oxo-5-phenyl-1H-1,4-benzodiazepin-3-yl]-3-(3-chlorophenyl)propanamide.

e. (3RS )-3-cyclohexyl-N-(2,3-dihydro-1-methyl-5-phenyl-2-thioxo-1H-1,4-benzodiazepin-3-yl)propanamide.

f. (−)-3-Carbohexyl-N-[(3R)-2,3-dihydro-1-methyl-2-oxo-4-oxido-5-phenyl-1H-1,4-benzodiazepin-3-yl] propanamide.

g. (+)-N-[2,3-dihydro-1-methyl-2-oxo-5-phenyl-1H-1,4-benzodiazepin-3-yl]-hexamamide.

h. (+)-N-[2,3-dihydro-1-methyl-2-oxo-5-phenyl-1H-1,4-benzodiazepin-3-yl]-pentanamide.

i. N-[2,3-Dihydro-1-methyl-2-oxo-5-isopropyl-1H-1,4-benzodiazepin-3-yl]-3-cyuclohexyl]propanamide.

j. N-[2,3-dihydro-1-methyl-2-oxo-5-isopropyl-1H-1,4-benzodiazepin-3-yl]-3-(2,4-dichlorophenyl)propanamide.

k. E-(+)-N-[(3R)-2,3-Dihydro-1-methyl-2-oxo-5-phenyl-1H-1,4-benzodiazepin-3-yl]-3-(4-methoxyphenyl)-2-propenamide.

l. (+)-N-[(3R)-2,3-Dihydro-1-methyl-2-oxo-5-phenyl-1H-1,4-benzodiazepin-3-yl]propanamide.

m. (+)-3-Cyclohexyl-N-[(3R)-2,3-dihydro-1-methyl-2-oxo-5-phenyl-1H-1,4-benzodiazepin-3-yl]propanamide.

n. (+)-N-[(3R)-2,3-Dihydro-1-methyl(-2-oxo-5-phenyl-1H-1,4-benzodiazepin-3-yl]-2-(2,4-dichlorophenylthio)acetamide.

o. (+)-N-[(3R )-7-Amino-2,3-dihydro-1-methyl-2-oxo-5-phenyl-1H-1,4-benzodiazepin-30-yl]-3-(2,4-dichlorophenyl)propanamide.

p. (+)-N-[(3R)-2,3-Dihydro-1-methyl-2-oxo-5-phenyl-1H-1,4-benzodiazepin-3-yl]-4-phenylbutanamide.

q. (+)-N-[(3R)-2,3-Dihydro-1-methyl-2-oxo-5-phenyl-1H-1,4-benzodiazepin-3-yl]-5-methyl-3-phenylisoxazole-4-carboxamide.

r. N-[2,3-Dihydro-1 -methyl-2-oxo-5-(4-methoxyphenyl)-1H-1,4-benzodiazepin-3-yl]-3-[2,4-dichlorophenyl]propanamide.

s. N-[2,3-Dihydro-1-methyl-2-oxo-5-ethyl-1H-1,4-benzodiazepin-3-yl}-3-(2,4-dichlorophenyl)propanamide.

t. E-(+)-N-[(3R )-2,3-Dihydro-1-methyl-2-oxo-5-phenyl-1H-1,4-benzodiazepin-3-yl]-3-(2,4-dichlorophenyl)-2-propeneneamide.

The utility of the exemplified compounds as anti-arrhythmic agents is shown by the following voltage-clamp and action potential studies in guinea pig isolated ventricular myocytes in vitro and by studies in conscious and anesthetized dogs in vivo. Although several of these compounds exhibit CCK antagonist activity, their antiarrhythmic activity stems primarily from block of the IKs current.

By block of the IKs current is meant a reduction in the amplitude of the time-dependent net outward current as measured in an isolated guinea pig myocyte and elicited during voltage clamp of the cell from a holding potential of −50 mV to +50 mV for 1 second under the conditions defined in the methods in Section I. below. Current amplitude is measured as the difference from the initial instantaneous current level following the capacitance discharge after changing the transmembrane voltage from −50 mV to +50 mV, to the current level at the end of the 1 second voltage step. Normally, an increase in the current amplitude occurs as a function of time and voltage during depolarization of the cardiac cell membrane and this increasing current has been defined as the delayed rectifier $K^+$ current ($I_K$). Cellular electrophysiologic studies have demonstrated that $I_K$ consists of two pharmacologically and kinetically distinct $K^+$ current subtypes, $I_{Kr}$ (rapidly activating and deactivating) and $I_{Ks}$ (slowly activating and deactivating). $I_{Ks}$ current occurs as a consequence of time- and voltage-dependent opening of ionic channels or pores in the cardiac cell membrane that allow the relatively selective flow of potassium ions ($K^+$) from the inside to the outside of the cell, that is, down the voltage and concentration gradient for $K^+$ions that is inherent in cardiac cells. Thus, block of the $I_{Ks}$ current ultimately reflects block of certain ion channels or pores in the cardiac cell membrane. However, the single pores or channels thought to underlie the $I_{Ks}$ current have yet to be measured or identified at the single channel level.

By selective block of $I_{Ks}$ is meant, compounds which block the $I_{Ks}$ current measured in isolated myocytes by 50% at a concentration of 1 μM or less ($IC_{50}$) and the concentration that blocks $I_{Ks}$ by 50% is at least 10 fold lower than the concentration required to cause 50% block of $I_{Kr}$ and/or $I_{K1}$.

I. VOLTAGE CLAMP MEASUREMENT OF IONIC CURRENTS AND ACTION POTENTIALS IN VITRO

METHODS:

Cell preparation:

Guinea pig ventricular myocytes were isolated using a modification of the procedure described by Mitra, R. and Morad, M., "A Uniform Enzymatic Method for Dissociation of Myocytes from Hearts and Stomachs of Nertilorates", Am. J. Physiol. 249:H105–660 (1985). Excised hearts were perfused through the aorta (retrograde fashion) at a rate of 10 ml/min with oxygenated, warmed (37° C.) solutions described below. The heart was initially perfused for 7 minutes with a Tyrode's solution containing, in mM: 132 NaCl, 4 KCl, 1.2 $MgCl_2$, 10 HEPES (formal name N-2-Hydroxyethylpiperazine-N-2-ethanesulfonic acid), 5 glucose, pH =7.2. The heart was then perfused with the same nominally $Ca^{2+}$-free solution containing 150 units/ml Type II collagenase (Worthington) and 0.5 units/ml Type XIV protease (Sigma) for 8 minutes. This perfusate was followed by a Tyrode's solution containing 0.2 mM $CaCl_2$ (without enzymes) for 5 minutes. The digested ventricles were cut into small pieces and gently shaken until cells were visibly dispersed. The cells were stored at room temperature until use, within 8 hours after isolation.

Microelectrode fabrication:

The suction microelectrode technique described by Giles, W. R. and Shibata, E. F., "Voltage clamp of bull-frog cardiac pacemaker cells: a quantitative analysis of potassium currents". J. Physiol. 368:265–292 (1985) was used to voltage clamp the cells. Microelectrodes were made by using a two stage puller from square bore (1.0 mm o.d.) borosilicate capillary tubing. Pipettes were filled with 0.5M K gluconate, 25 mM KCl and 5 mM $K_2ATP$. The electrodes had resistances of 3 to 7 Mohm when filled with this solution. After establishing whole-cell recording mode, negative pressure was maintained on the pipette using a 1 ml gas-tight syringe attached via air tight tubing to the suction port of the microelectrode holder. This minimized dialysis of the cell with the pipette solution.

Voltage-clamp technique:

To record $K^+$ currents, the cells were bathed in a $Ca^{2+}$-free Tyrode's solution containing 0.4 mM nisoldipine. Nisoldipine is a relatively specific blocker of L-type $Ca^{2+}$ channels, having no effect on $K^+$ currents at this concentration (Kass, R. S., "Nisoldipine: a new, more selective calcium current blocker in cardiac Purkinje fibers", J. Pharmacol. Exp. Ther. 223:446–456, 1982). To record $Ca^{2+}$ currents, the cells were bathed in Tyrode's solution containing 1.8 mM $Ca^{2+}$ without nisoldipine. The cell chamber was superfused with solutions at a rate of 1–2 ml/minute, while maintaining the temperature at 35°±1° C. A List EPC-7 clamp amplifier was used to voltage clamp the isolated cells. Series resistance was compensated 40–70%, and current was low-pass filtered at a cut-off frequency of 1 kHz. Data acquisition and analysis were performed using pClamp software (Axon Instruments, Burlingame, Calif.) and either an AST 286 or a Compaq 386 computer. A variety of voltage pulse protocols were used to measure $Ca^{2+}$ current and three types of $K^+$ currents: inward rectifier ($I_{K1}$), rapidly activating delayed rectifier ($I_{Kr}$) and the slowly activating delayed rectifier ($I_{Ks}$). Sanguinetti, M. C. and Jurkiewicz, N. K., "Two components of cardiac delayed rectifier $K^+$ current: Differential sensitivity to block by Class III antiarrhythmic agents". J. Gen Physiol 96:194–214, 1990. Data was analyzed as % block from control membrane currents.

Current-clamp technique:

To record action potentials, single cells were bathed in 1.8 mM $Ca^{2+}$-Tyrode's solution. The cell chamber was supefused with solutions at a rate of 1–2 ml/minute, while maintaining the temperature at 35°±1° C. A List EPC-7 clamp amplifier was used to current-clamp the cells. Action potentials were elicited at a frequency of 0.2 Hz with 1 nA current pulses of 2 msec duration. Data were analyzed as percent (%) change in action potential duration at 90% of repolarization ($APD_{90}$).

Solutions:

Nisoldipine was prepared as a 4 mM stock solution in polyethylene glycol 200. Compounds tested in this series were prepared as 10 mM stock solutions in polyethylene glycol 400 or dimethyl sulfoxide. At the final concentrations used neither polyethylene glycol 200, 400 nor dimethyl sulfoxide had any effect on membrane currents.

Results:

As an example of this series of compounds, compound number 4 in the foregoing list of preferred compounds exhibited a concentration dependent block of $I_{Ks}$ with an $IC_{50}$ of 215 nM. Complete block of $I_{Ks}$ was observed at 5 µM. Little or no effect was seen on $I_{K1}$ (1 µM), $I_{Kr}$ (1 µM) or $I_{Ca}$ (0.1 µM) at the indicated concentrations. $IC_{50}$ for $I_{Kr}$ was estimated to be approximately 5 µM. Action potentials elicited from 4 cells exposed to 5 µM Of compound number 4 exhibited an increase in $APD_{90}$ of 202+85%.

II. ELECTROCARDIOGRAPHIC QT INTERVAL IN CONSCIOUS DOGS

Methods:

Trained, female mongrel dogs, in the weight range of 8 to 16 kg and instrumented with chronic arterial access ports, were deprived of food 18 to 24 hours prior to the study. At test time, the dog was placed in an Alice King Chatham nylon mesh sling for light restraint. Four Grass Instrument Co. Type E2 Platinum Subdermal Electrodes were affixed to the limbs of the dog and connected to a Hewlett-Packard 4700A Cardiograph multi-lead electrocardiogram (ECG) recorder. After approximately a 30-minute stabilization period, one or two pretreatment Lead II ECG tracings were taken over approximately a 30-second interval. Dogs were then dosed via gavage with labrafil (vehicle) or test compound. The volume administered was 2.0 ml/kg followed by a 15 ml tap-water flush. Lead II ECG recordings were obtained at 15, 30, and 60 minutes and every 30 minutes thereafter for five hours post-drug administration. Dogs were also monitored for blood pressure changes via a Modular Instruments data acquisition system and transducer connected to the arterial access port. Final ECG traces were taken at approximately 24 hours post-treatment. Average QT interval lengths were determined for each time point and $QT_c$ values were calculated to correct for variations in heart rate ($QT_c = QT/\sqrt{R-R}$).

As an example of this series of compounds, oral administration of compound number 4 elicited a dose-related prolongation of ECG QT interval. There were no other ECG or cardiovascular effects of compound number 4 in conscious dogs.

III. FREQUENCY-DEPENDENCE OF CLASS III ACTIVITY

The propensity for Class III antiarrhythmic agents that predominantly block $I_{Kr}$ to cause arrhythmia at slow heart rates is likely due to the "reverse frequency-dependent" action of these agents, that is, these agents have greater activity at slow vs fast heart rates (Hondeghem, L. M. and Snyders, D. J., "Class III antiarrhythmic agents have a lot of potential, but a long way to go: reduced effectiveness and dangers of reverse use-dependence", Circulation 81: 686–690, 1990; Hondeghem, L. M.,"Development of Class III antiarrhythmic agents", J. Cardiovasc. Pharmacol. (Suppl 2): S17–S22, 1992; Funck-Brentano, C., "Rate-dependence of Class III actions in the heart". Fundam. Clin. Pharmacol. 7: 51–59, 1993). Cellular electrophysiologic studies indicate that the reverse frequency-dependent profile, Class III agents that block $I_{Kr}$ is the result of a diminished contribution of the $I_{Kr}$ current, relative to other outward currents (eg., $I_{Ks}$), to repolarization at fast heart rates (Jurkiewicz N. K. and Sanguinetti, M. S. "Rate-dependent prolongation of cardiac action potentials by a methanesulfonanilide Class III antiarrhythmic agent: specific block of rapidly activating delayed rectifier $K^+$ current by dofetilide", Circ. Res. 72, 75–83, 1993). Because $I_{Ks}$ may contribute more to repolarization at faster heart rates, the selective blockade of $I_{Ks}$ represents a potential target for safer and more effective Class III antiarrhythmic agents. First, a selective blocker of $I_{Ks}$ should not display exaggerated activity at slow heart rates, and would therefore possess a more favorable safety profile than reverse frequency-dependent $I_{Kr}$ blocker Class III antiarrhythmic agents. Second, a selective blocker of $I_{Ks}$ should possess equal or greater activity at faster heart rates which might result in greater efficacy against arrhythmias. The in vitro cellular electrophysiologic studies and in vivo cardiac electrophysiologic studies in anesthetized dogs described below were conducted in order to test the hypothesis that the selective blockade of $I_{Ks}$ would result in either frequency-independent (i.e., equivalent activity at slow and fast rates) or forward frequency-dependent (greater activity at faster vs slower rates) Class III activity.

III. A. FREQUENCY-DEPENDENT EFFECTS ON ACTION POTENTIAL DURATION IN VITRO IN ISOLATED VENTRICULAR MYOCYTES

Methods

Cell preparation: Same as described in section I.
Action Potential Measurements:

Transmembrane action potential measurements were made using a technique similar to that described previously by Salata, J. J. and Wasserstrom, J. A. "Effects of quinidine on action potentials and ionic currents in isolated canine ventricular myocytes", Circ. Res. 62:324–337, 1988. The isolated ventricular myocytes were transferred to a glass bottom experimental perfusion chamber (12×25 mm) filled with a HEPES-Tyrode's solution containing in mM: 132 NaCl, 4 KCl, 1.8 $CaCl_2$, 1.2 $MgCl_2$, 10 HEPES, 5 glucose, pH =7.2 to a height of 2 mm. After the myocytes settled to the bottom of the chamber, they were continuously superfused with preheated HEPES-Tyrode's solution at a rate of 2.0 ml/min. The temperature was monitored and maintained at 36°±0.5° C. The experimental chamber was placed on the stage of an inverted microscope (Nikon Diaphot-TMD) to view the cells. Transmembrane potentials were recorded by means of conventional glass microelectrodes that were filled with 3M KCl and had tip resistances of 40–60 MΩ. The microelectrode was connected through a Ag—AgCl electrode to the headstage preamplifier (model HS-2, gain=1.0) of an operational amplifier with a high input impedance and variable input capacitance neutralization (Axoclamp-2A, Axon Instruments, Foster City, Calif.). The voltage drop across the microelectrode produced by current injection was compensated electronically with an active bridge circuit immediately before impalement of a cell. The experimental bath was grounded through a 3M KCl agar bridge and a Ag—AgCl junction. The microelectrodes were positioned carefully at the cell surface using a hydraulic micromanipulator (Narishige Model MO-303, Greenvale, N.Y.). Penetration of the cell membrane was achieved by briefly (1–3 msec) increasing the input capacitance neutralization to cause oscillation of the amplifier. After establishing a stable microelectrode seal, the myocyte was lifted off the bottom of the chamber to allow complete superfusion of the cell. Action potentials were generated by passing current pulses of 1 msec in duration, and with an intensity of 1.2 times threshold at varying stimulus rates through the recording electrode. Cells were allowed to stabilize for 20 minutes before collection of data began. Voltage signals were digitized using an analog to digital converter (TL-1, DMA interface, Axon Instruments, Foster City, Calif.) at a sampling frequency of 2 kHz. Data acquisition and analysis were performed with pClamp software (Axon Instruments, Foster City, Calif.) and an AST 486 computer (Irvine, Calif.).

Action potentials were stimulated at rates of either 60, 120, and 180 beats/min and were allowed to stabilized for 1 minute at each rate. Trains of stimuli were applied at each of these rates for a duration of 30 seconds and the last action potential of the train was recorded from each of 5 trains and these 5 action potentials were averaged. Action potential duration at 90% of repolarization ($APD_{90}$)was measured from the averaged action potential traces at each stimulus rate in control and at 10 minutes after superfusion of solution containing the compound of Example 26 at a given concentration. The compound was superfused at sequentially increasing concentrations. The compound of Example 26 was dissolved at a stock concentration of 1 mM in dimethyl sulfoxide (DMSO) and diluted directly into HEPES Tyrode's solution using serial dilutions as necessary to achieve final test concentrations.

Results

In these studies, one of the preferred compounds, the compound of Example 26, produced both concentration and rate-dependent increases in the action potential duration of isolated guinea pig myocytes as shown in Table 1. In the control, $APD_{90}$ values were 229±22, 206±15, and 189±10 msec at stimulus rates of 60, 120, and 180 beats/min, respectively. The compound of Example 26, at 10 nM, increased $APD_{90}$ more at fast vs slow rates. For example, $APD_{90}$ was increased an average of 12.4% at 180 beats/min vs 9.4% at 60 beats/min. Thus, at lower concentrations the compound increased $APD_{90}$ in a forward frequency-dependent manner. At higher concentrations, $APD_{90}$ was increased equally at fast and slow rates. The percent increases were not statistically different at the different stimulus rates, therefore, at higher concentrations $APD_{90}$ was increased in a frequency-independent manner. The increases in $APD_{90}$ were nearly completely reversible after 20 min of washout of the compound.

TABLE 1

E-(+)-N-[(3R)-2,3-Dihydro-1-methyl-2-oxo-5-phenyl-1H-1,4-benzodiazepin-3-yl]-3-(2,4-dichlorophenyl)-2-propeneneamide:Concentration- and Frequency-Dependent Increases in Action Potential Duration at 90% of Repolarization ($APD_{90}$) in Isolated Ventricular Myocytes.

| STIMULUS Concentration [nM] | Rate beats/min | $APD_{90}$ % Change | SEM |
|---|---|---|---|
| 10 | 60 | 9.4 | ±2.4 |
| | 120 | 10.1 | ±1.2 |
| | 180 | 12.4 | ±3.4 |
| 30 | 60 | 16.0 | ±2.3 |
| | 120 | 14.8 | ±1.3 |
| | 180 | 14.4 | ±1.8 |
| 100 | 60 | 24.7 | ±4.4 |
| | 120 | 24.3 | ±4.4 |
| | 180 | 22.9 | ±4.0 |
| Washout | 60 | 4.2 | ±6.3 |
| | 120 | 5.3 | ±5.1 |
| | 180 | 5.9 | ±3.9 |

Data are Mean ± SEM (n ≥ 5 cells)

III.B FREQUENCY—DEPENDENT EFFECTS ON CARDIAC REFRACTORY PERIOD IN VIVO IN ANESTHETIZED DOGS

Methods. Purpose-bred male or female mongrel dogs (9.8–10.8 kg) were anesthetized with alpha chloralose (80–100 mg/kg i.v.), and the animals were ventilated using a volume-cycled respirator. The right femoral artery and vein were isolated and cannulated for the measurement of systemic arterial pressure and for test agent administration, respectively. A right thoracotomy was performed in the 4th intercostal space, the pericardium incised, and the heart suspended in a pericardial cradle. One stainless steel bipolar plunge electrode was sutured to the anterior surface of the right ventricle for the determination of ventricular excitation threshold and refractory periods, while a second stainless steel bipolar plunge electrode was sutured to the right ventricular apex for ventricular pacing. A 21 gauge stainless steel hypodermic needle attached to a 1 ml syringe containing 40% formaldehyde was introduced into the right atrium via a stab wound and purse-string suture. The atrioventricular (AV) node was identified and then chemically ablated with formaldehyde using the method of Steiner and Kovalik (Steiner, C. and Kovalik, A. T. W., "A simple technique for production of chronic complete heart block in dogs", J. Appl. Physiol. 25: 631–632, 1968). After the ablation of the AV node, heart rate was controlled and maintained at either 60 or 150 beats/min, as dictated by the experimental protocol, by ventricular apical pacing. Limb electrodes were attached for the continuous recording of Lead II electrocardiogram.

Ventricular excitation threshold (ET) and relative refractory periods (RRPs) were determined alternately at heart rates of 60 and 150 beats/min using an extrastimulus technique described previously (Wallace, A. A. et. al.,"Cardiac electrophysiologic and inotropic actions of new and potent methanesulfonanilide Class III antiarrhythmic agents in the anesthetized dog". J. Cardiovasc. Pharmacol. 18: 687–695, 1991). Ventricular excitation threshold was defined as the minimum current required to evoke a propagated response for a ventricular extrastimulus introduced at a coupling interval of 250–300 msec after a basic ventricular apical beat. The ventricular relative refractory period was defined as the longest coupling interval failing to elicit a propagated response for a ventricular extrastimulus introduced with a current intensity of 2× the ventricular excitation threshold. Multiple alternating baseline 60 and 150 beat/min RRPs were measured in each preparation, with two-to-three stable consecutive baseline RRP determinations required prior to administration of the test agent.

In this study, one of the preferred compounds, E-(+)-N-[(3R)-2,3-Dihydro-1-methyl-2-oxo-5-phenyl-1H-1,4-benzodiazepin-3-yl]-3-(2,4-dichlorophenyl)-2-propeneneamide, (Compound of Example 26) was used as an example of a selective blocker of $I_{Ks}$. The compound of Example 26 was administered intravenously at a dosage of 1.0 mg/kg over a period of 5 minutes to a group of 5 anesthetized dogs. The compound of Example 26 was infused in a vehicle of 2% cremophor/2% ethanol/96% saline, at a test agent concentration of 0.5 mg/ml. Ventricular RRPs at 60 and 150 beats/min were redetermined immediately, 15 and 30 minutes following the intravenous administration of the compound of Example 26. The frequency-dependence of the activity of the compound of Example 26 was assessed by comparing absolute increases in ventricular RRPs from the final corresponding baseline value determined at slower (60 beat/min) vs faster (150 beat/min) heart rates.

Results

The table below summarizes the absolute increases in the ventricular RRP from the respective baseline values observed at slower (60 beat/min) vs faster (150 beat/min) heart rates after the intravenous administration of 1.0 mg/kg of the compound of Example 26. Equivalent increases in the ventricular RRPs were observed at the 60 and 150 beat/min heart rates following the administration of the compound of Example 26, indicating that it displays "frequency-independent" activity to increase the RRP.

TABLE 2

Increase in Ventricular Relative Refractory Period (msec) Above Baseline Following the Intravenous Administration of 1.0 mg/kg of the compound of Example 26 at Indicated Heart Rate and Time Points after Infusion

| Heart Rate (Beat/Min) | Immediate | 15 Min | 30 Min |
|---|---|---|---|
| 60 | 29.6 ± 4.4 | 19.2 ± 3.4 | 14.0 ± 2.3 |
| 150 | 23.2 ± 7.3 | 15.6 ± 4.1 | 11.4 ± 4.4 |

Data are Mean ± S.E.M.; n = 5

The compounds of the present invention have the pharmacological properties required for the antiarrhythmic agents of Class III, namely the prolongation of the myocardial action potential in vitro without a significant depression of the Vmax or prolongation of cardiac refractory period or $QT_C$-interval in dogs. Moreover, the effects of many of the novel compounds, in contrast to such $I_{Kr}$ blockers, increase action potential duration equally or to a greater extent at fast heart rates. These compounds are much more potent than the reference drug, sotalol.

The compounds of the present invention are effective in treating and preventing all types of arrhythmias including ventricular and atrial (supraventricular) arrhythmias. The compounds of the present invention are especially useful to control reentrant arrhythmias and prevent sudden death due to ventricular fibrillation.

In the novel method of treating arrhythmia of this invention, a compound or pharmaceutically acceptable salt thereof, is administered in an amount ranging from about 0.01 to about 50 mg per kg of body weight per day, preferably from about 1.0 to about 30 mg per kg of body weight per day in a single dose or in 2 to 4 divided doses.

The compounds of this invention can be administered as the sole active ingredient or in combination with other antiarrhythmic agents or other cardiovascular agents.

The compounds, or pharmaceutically acceptable salts thereof, of the present invention, in the described dosages, are administered orally, intraperitoneally, subcutaneously, intramuscularly, transdermally, sublingually or intravenously. They are preferably administered orally, for example in the form of tablets, troches, capsules, elixirs, suspensions, syrups, wafers, chewing gum, or the like prepared by art recognized procedures. The amount of active compound in such therapeutically useful compositions or preparations is such that a suitable dosage will be obtained.

The following examples illustrate the present invention without, however, limiting the same thereto.

EXAMPLE 1

Following the protocol described previously but substituting the compounds listed below for compound number 4, the following results are obtained:

| No. of Compound | IC$_{50}$ or % Block (μM) | | IC$_{50}$ (mM) | |
|---|---|---|---|---|
| | Guinea Pig Myocytes | | | |
| | IKs | IKr | CCKA | CCKB |
| 1 | 0.220 | 20% (1) | 8.0 | 3,800 |
| 2 | 25% (1) | 21% (1) | 0.07 | 220 |
| 5 | 57 | 77 | >3 mM 2% | >3 mM 0% |

| | | | | |
|---|---|---|---|---|
| 8 | 10 | 38 | — | — |
| 9 | 20 | 93 | — | — |

Cellular Electrophysiology (% Block)

| Conc. | $I_{Kl}$ | $I_{Kr}$ | $I_{Ks}$ |
|---|---|---|---|
| 5 | 1 μM | n = 2<br>1.6 | n = 6<br>16.1 | n = 2<br>10 |
| | 10 μM | n = 5<br>5.2 ± 1.8 | n = 5<br>24.7 ± 13 | n = 5<br>30.5 ± 6.6 |
| 7 | 1 μM | n = 4<br>6.5 ± 2. | n = 4<br>14.8 ± 6.7 | n = 6<br>29.9 ± 6 |
| | 10 μM | n = 4<br>8.6 ± 2.2 | n = 4<br>36.4 ± 2.9 | n = 4<br>43.4 ± 10.8 |

Cellular Electrophysiology (% Block)

| Conc. | $I_{Kl}$ | $I_{Kr}$ | $I_{Ks}$ |
|---|---|---|---|
| 9 | 1 μM | n = 2<br>2 | n = 2<br>44.3 | n = 2<br>20 |
| | 10 μM | n = 2<br>0.6 | n = 2<br>82.4 | n = 2<br>66 |
| 12 | 1 μM | n = 4<br>8 ± 2.4 | n = 4<br>13 ± 3.1 | n = 4<br>146.5 |
| | 10 μM | n = 4<br>10 ± 4.2 | n = 4<br>30 ± 5.4 | n = 4<br>16 ± 11 |

EXAMPLE 2

N-[3(R,S)-5-Cyclohexyl-2,3-dihydro-1-methyl-2-oxo-1H-1,4-benzodiazepin-3-yl]N'-[3-(isopropylsulfonyl amino carbonyl)phenyl]urea Step 1: Isopropylsulfonamide Ammonia gas was bubbled through a stirred solution of isopropylsulfonyl chloride (3.9 ml, 35 mmol) in anhydrous tetrahydrofuran (100 ml), cooled to 0° C., for 30 minutes. After allowing to warm to ambient temperature, the mixture was filtered and the filtrate evaporated in vacuo, to leave a white solid. This was partitioned between ethyl acetate (50 ml) and water (50 ml). The organic phase was separated and the aqueous phase extracted with ethyl acetate (3×50 ml). The combined organic layers were dried ($Na_2SO_4$) and evaporated in vacuo to afford the title compound (3.5 g, 81%) as a colorless solid, mp 51°–53° C. 1H NMR (360 m Hz, $CDCl_3$ ) w1.92 (6H, d, J 32 6.7 Hz), 3.22 (1H, septet, J=6.7 Hz), 4.61 (2H, br s).

Step 2: 1-(Isopropylsulfonylaminocarbonyl)-3-nitrobenzene

To a mixture of isopropylsulfonamide (1.7 g, 13.8 mmol), 3-nitrobenzoic acid (2.31 g, 13.8 mmol) and 4-dimethylaminopyridine (1.69 g, 13.8 mmol)in anhydrous dichloromethane (100 ml) under an atmosphere of nitrogen was added 1-[3-(dimethylamino)-propyl]-3-ethyl carbodiimide hydrochloride (2.65 g, 13.8 mmol). The mixture was stirred at ambient temperature for 20 hours, then extracted with 1M NaOH and the separated aqueous phase was acidified using 5M HCl. The solid which precipitated was collected by filtration, washed with water and dried under vacuum to afford the title compound (2.74 g, 75%) as a colorless solid, mp 175°–177° C. 1H NMR (360 MHz, $D_6$-DMSO) w1.34 (6H, d, J=6.9 Hz), 3.83 (1H, septet, J=6.9 Hz), 7.93 (1H, dd, J=8.0 and 8.0 Hz), 8.35 (1H, d, J=8.0 Hz), 8.48 (1H, d, J=8.0 Hz), 8.78 (1H, s), 12.40 (1H, br s).

Step 3: 1-(Isopropylsulfonylaminocarbonyl)3-aminobenzene

To a suspension of 1-(isopropylsulfonylaminocarbonyl)nitrobenzene (2.5 g, 9.2 mmol)in ethanol (50 ml) was added 10% palladium on carbon (0.25 g, 10% (w/w)) in water (2 ml). The mixture was hydrogenated at 40 psi for 10 minutes after which the catalyst was filtered off and washed with ethanol. The solvents were evaporated in vacuo to give the title compound was afforded as a yellow solid. This was recrystallised from hot ethanol to give a pale yellow crystalline solid (1.7 g 75%), mp 190°–193° C. 1H NMR (360 MHz, $D_6$-DMSO) w1.30 (6H, d, J=6.8 Hz), 3.79 (1H, septet, J=6.9 Hz), 5.36 (2H, br s), 6.79 (1H, dd, J=7.9 and 1.2 Hz), 7.05 (2H, m), 7.13 (1H, dd, J=7.8 and 7.8 Hz).

Step 4: N-3-(R,S)-5-Cyclohexyl-2,3-dihydro-1-methyl-2-oxo-1H-1,4-benzodiazepin-3-yl] N'-[3-(isopropylsulfonylaminocarbonyl)phenyl]urea A solution of 5-cyclohexyl-1,3-dihydro-1-methyl-3(R,S)-[4-nitrophenyloxycarbonyl)-amino]-2H-1,4-benzodiazepin-2-one (0.3 g, 0.69 mmol) in anhydrous dimethyl formamide (6 ml) and 1-(isopropyl-carbonylaminosulfonyl)-3-aminobenzene (0.175 mg, 0.72 mmol) was added dropwise. After recrystallization from hot ethanol the compound (0.24 g, 65%) was afforded as a colorless solid, mp 165° C. (dec.). 1H NMR (360 MHz, $D_6$-DMSO) w0.87–0.98 (1H, m), 1.10–1.64 (7H, m), 1.30 (6H, d, J=6.9 Hz), 1.79 (1H, m), 1.88–1.96 (1H, m), 2.95 (1H, m), 3.33 (3H, s), 3.79 (1H, septet, J=6.9 Hz), 5.07 (1H, d, J=8.2 Hz), 7.37 (3H, m), 7.46 (1H, d, J=7.8 Hz), 7.55 (2H, m), 7.64 (1H, dd, J=7.1 and 7.1 Hz), 7.75 (1H, d, J=7.9 Hz), 7.92 (1H, s), 9.22 (1H, s), 11.93 (1H, br s).

EXAMPLE 3

Other compounds which exemplify the treatment of arrhythmia through blockade of the IKs channel include, but are not limited to the following:

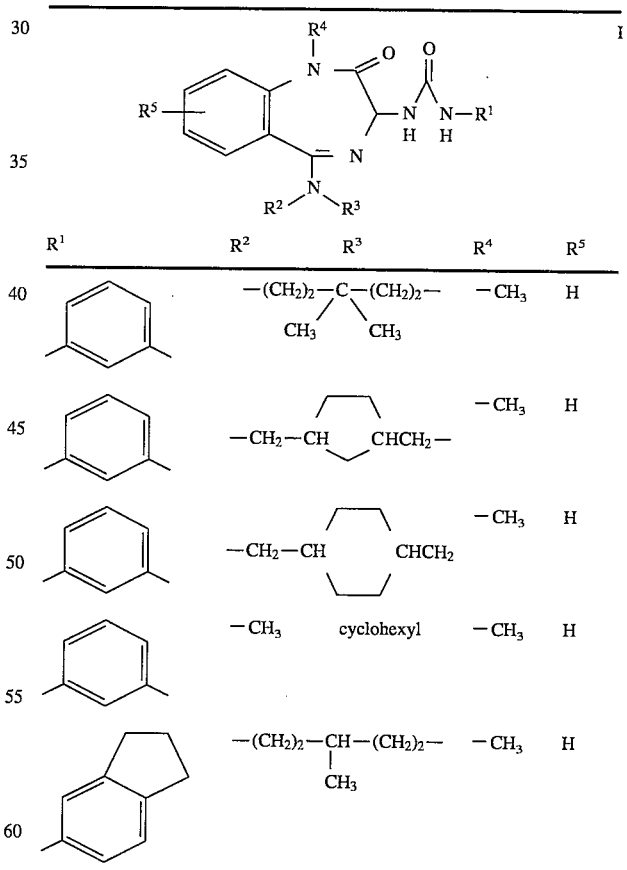

N-[3(RS)-5-(N-Cyclohexyl-N-methylamino)-2,3-dihydro-1-methyl-2-oxo1H-1,4-benzodiazepin-3-yl]-N'-[3-methylphenyl]urea Step A: Preparation of Methyl-2-(N-bromoacetyl-N-methylamino) benzoate A solution of bromoacetyl bromide (209 g, 1.03 mol) in dichloromethane (200 ml) was added dropwise to a cooled (ice bath) solution of methyl N-methylanthranilate (158 g, 0.96 mol) in dichloromethane (1.41). A solution of sodium hydroxide (59 g, 1.47 mol) in water (400 ml) was added dropwise to this ice cold solution then after addition the reaction mixture was stirred at room temperature for 20 hours. The organic phase was separated and washed with 1M hydrochloric acid (500 ml), brine (300 ml), saturated sodium hydrogen carbonate solution (400 ml), dried (sodium sulphate) then evaporated to afford the required product as a solid (255 g, 92%). $^1$H NMR (360 MHz, CDCl$_3$) δ3.23 (3H, s), 3.54 (1H, d, J=11 Hz), 3.60 (1H, d, J=11 Hz), 3.90 (3H, s), 7.40 (1H, d, J=8 Hz), 7.51 (1H, dd, J$_1$=J$_2$=8 Hz), 7.65 (1H, dd, J$_1$=J$_2$=8 Hz), 8.04 (1H, d, J=8 Hz).

Step B: Preparation of 2,5-Dioxo-1-methyl-1,4-benzodiazepine

Ammonia gas was bubbled through an ice-cooled solution of methyl 2-(N-bromoacetyl-N-methylamino)benzoate (255 g, 0.89 mol) in methanol (1.61) until saturated. The cooling bath was removed and the reaction mixture left standing at room temperature for 18 hours. The precipitate was collected to afford the required product (79 g). The filtrate was evaporated and the residue partitioned between dichloromethane (300 ml) and 10% citric acid solution (200 ml). The organic layer was separated, washed with brine (200 ml), dried (sodium sulphate) then evaporated to give a solid which was recrystallized from dichloromethane/petroleum ether (60–80) to afford further product (32.5 g). Total yield=111.5 g (73%). Mp 190°–193° C. $^1$H NMR (360 MHz, CDCl$_3$) δ3.42 (3H, s), 3.80 (2H, broad s), 6.80 (1H, s), 7.24 (1H, d, J=8 Hz), 7.32 (1H, dd, J$_1$=J$_2$=8 Hz), 7.57 (1H, dd, J$_1$=J$_2$=8 Hz), 7.90 (1H, d, J=8 Hz). Found C, 63.20; H, 5.25; N, 14.77. C$_1$H$_{10}$N$_2$O$_2$ requires C, 63.15; H, 5.30; N, 14.73%.

Step C:

The desired product was prepared as for Example 1 parts a, b, and c, using 2,5-dioxo-1-methyl-1,4-benzodiazepine in place of 2,5-dioxo-1-propyl-1,4-benzodiazepine to give a white solid which was recrystallized from methanol, water to give the desired product (70 mg). Mp 145°–147° C. $^1$H NMR (360 MHz, D$_6$-DMSO) δ0.99 (10H, m), 2.21 (3H, s), 2.65 (3H, s), 3.31 (4H, m), 4.92 (1H, d, J=8.4 Hz), 6.70 (1H, d, J=8.0 Hz), 6.93 (1H, d, J=7.5 Hz), 7.09 (2H, m), 7.17 (1H, s), 7.36 (1H, m), 7.49–7.69 (3H, m), 8.80 (1H, s); MS (CI) m/e 434 [MH]$^+$. Anal. Found C, 67.22; H, 7.23; N, 15.29. C$_{25}$H$_{31}$N$_5$O$_2$.0.75H$_2$O requires C, 67.17; H, 7.33; N, 15.67%.

EXAMPLE 4

(−)-N-[5-(N-Cyclohexyl-N-methylamino)-2,3-dihydro-2-oxo-1-methyl-1H-1,4-benzodiazepin-3-yl]-N'-[3-methylphenyl]urea Hydrochloride The desired product was separated from the racemate of Example 4 by chiral HPLC as for Example 2, Step A. Peak A (eluted first) was treated as for Example 2 part B and the free base obtained was dissolved in dichloromethane. Ethereal hydrogen chloride was added and after 5 minutes the solvent was removed in vacuo. The resulting oil was crystallized from dichloromethane/ether to give the desired hydrochloride as a white solid (100 mg). Mp 193°–195° C. $^1$H (360 MHz, D$_6$-DMSO, trifluoroacetic acid) δ0.95–1.95 (10H, m), 2.23 (3H, s), 3.12 (3H, s), 3.43 (4H, m), 5.39 (1H, m), 6.76 (1H, d, J=7.2 Hz), 7.11–7.90 (7H, m). MS (CI) m/e [MH]$^+$. Anal. Found. C, 60.45; H, 7.02; N, 14.05. C$_{25}$H$_{31}$N$_5$O$_2$.HCl. 1.5H$_2$O requires C, 60.41; H, 7.02; N, 14.35%, [α]$^{22}_D$ −195° (c=0.1, MeOH). Purity A:B=>99%.

EXAMPLE 5

(+)-N-[5-(N-Cyclohexyl-N-methylamino)-2,3-dihydro-2-oxo-1-methyl-1H-1,4-benzodiazepin-3-yl]-N'-[3-methylphenyl]urea Hydrochloride The desired product was separated from the racemate from Example 4 by chiral HPLC as for Example 2 part A. Peak B (eluted second) was treated as for Example 5 peak A to yield the desired hydrochloride (90 mg). Mp 194°–196° C. $^1$H NMR (360 MHz, D$_6$-DMSO+ trifluoroacetic acid) δ0.95–1.95 (10H, m), 2.24 (3H, s), 3.12 (3H, s), 3.43 (4H, m), 5.39 (1H, m), 6.76 (1H, d, J=7.5Hz), 7.06–7.86 (7H, m), 9.20 (1H, s); MS (CI) m/e 434 [MH]$^+$. Anal. Found. C, 58.28; H, 6.82; N, 13.47. C$_{25}$H$_{31}$N$_5$O$_2$.HCl.2.35H$_2$O requires C, 58.61; H, 7.22; N, 13.67%. [α]$^{22}_D$+154° (C=0.1, MeOH). Purity B:A=>95%.

Further examples of other compounds which are useful in the treatment of arrhythmia by blockade of the IKs current include but are not limited to compounds such as:

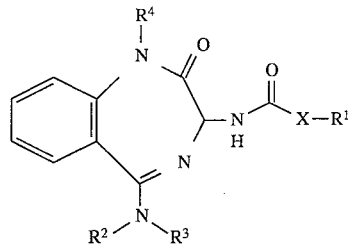

where X is —CH$_2$—, R$^1$ is 1-naphtyl, R$^2$ and R$^3$ taken together are —(CH$_2$)$_6$— and R$^4$ is n-propyl.

EXAMPLE 6

(±)-N-[2,3-dihydro-1-methyl-2-oxo-5-(N-cyclohexyl-N-methylamino)-1H-1,4-benzodiazepin-3-yl]-3-phenylpropanamide Step A:

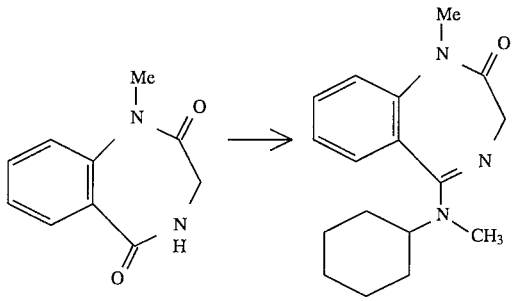

A solution of PCl$_5$ (6.6 g, 32 mmol) in 250 mL dichloromethane was added to a stirred solution of 1-methyl-1,4-benzodiaz-epine-2,5-dione (5.0 g, 26 mmol) in 150 mL of dichloromethane. The solution was stirred at room temperature for 3 hours before evaporation of volatiles. The resulting foam was dissolved in 200 mL dichloromethane, the solution cooled to 0° C. and a solution of N-methyl-cyclohexylamine (11.8 mL, 91 mmol) in 50 mL of dichloromethane added over 5 minutes. The reaction mixture was allowed to warm to room temperature, and partitioned. The organic phase was washed with brine, dried (MgSO₄) and solvent evaporated to give the product as a foam. Yield 6.9 g.

NMR (300 MHz, CDCl₃) δ: 7.60 (m, 1H), 7.47–7.52 (m, 2H), 7.33 (m, 1H), 4.0 (½AB, J=12.2 Hz, 1H), 3.47 (½AB, J=12.2 Hz, 1H), 3.35 (s, 3H), 3.3 (m, 1H), 2.78 (s, 3H), 1.0–2.0 (m, 10H).

Step B:

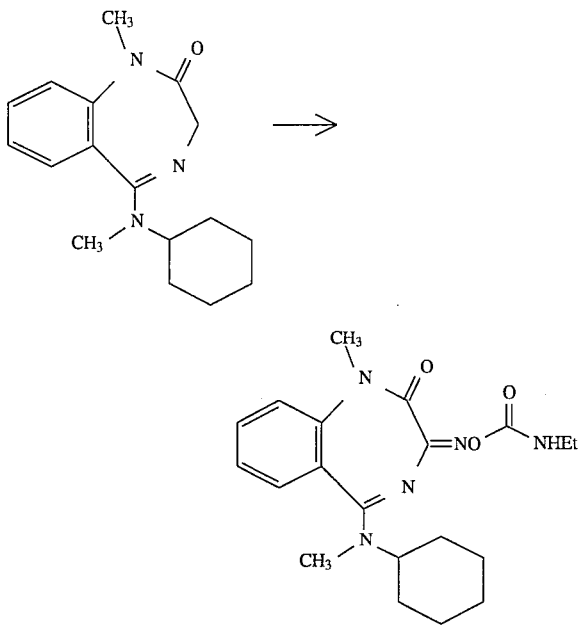

A solution of 2,3-dihydro-1-methyl-2-oxo-5-(N-cyclohexyl-N-methylamino)-1H-1,4-benzodiazepine (770 mg, 2.7 mmol) in 10 mL toluene was added to a stirred and cooled (30° C.) suspension of potassium t-butoxide (750 mg, 6.7 mmol) in 25 mL of toluene. After stirring at −30° C. for 30 minutes, isoamyl nitrite (540 μL, 4.0 mmol) was added and the reaction mixture stirred for 3 hours at −20° C. The mixture was then poured into 10% citric acid solution/ethyl acetate, stirred for 10 minutes, the pH adjusted to 7 with saturated potassium carbonate solution and the phases separated. The organic phase was washed with brine, the organic phase dried (MgSO₄) and the solvent evaporated to give a foam. This was dissolved in 15 mL THF and ethyl isocyanate (395 μL, 5 mmol) added followed by triethylamine (700 μL, 5 mmol). The reaction mixture was heated to 60° C. for 2 hours, cooled to room temperature, the volatiles evaporated and the residue purified by flash column chromatography (silica, 75% ethyl acetate/hexane) to afford 720 mg of product as a foam.

NMR (300 MHz, CD₃OD) δ: 7–7.6 (m, 5H), 3.5 (m, 1H), 3.42 (s, 3H), 2.7–3.3 (m, 5H), 1.1–2 (m, 10H), 1.05 (t, J=7 Hz, 3H).

Step C:

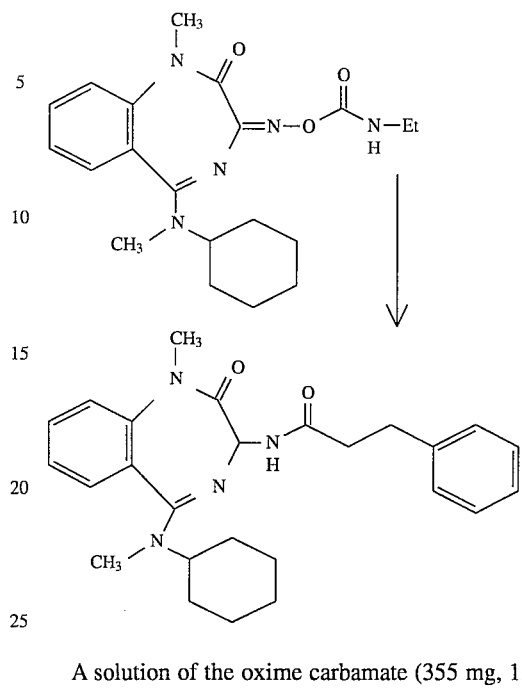

A solution of the oxime carbamate (355 mg, 1.85 mmol) in 30 mL methanol was hydrogenated at 50 psi over 300 mg of 10% palladium/charcoal for 3 hours. The mixture was filtered through celite and the filtrate evaporated to give the crude amine. This was dissolved in 5 ml DMF and phenylpropionic acid (300 mg, 2 mmol), 1-hydroxybenzotriazole hydrate (305 mg, 2 mmol), triethylamine (250 μL, 1.8 mmol) and 1-(3-dimethylaminopropyl)-3-ethylcarbodiimide (380 mg, 2 mmol) added. The reaction mixture was stirred at room temperature for 18 hours, poured into water and extracted with ethyl acetate. The organic phase was washed with sodium bicarbonate solution and brine, dried (MgSO₄) and solvent evaporated to give a solid, recrystallized from ethyl acetate/hexane to afford (±)-N-[2,3-Dihydro-1-methyl-2-oxo-5-(N-cyclohexyl-N-methylamino)-1H-1,4-benzo-diazepin-3-yl]-3-phenylpropanamide m.p. 167°–168° C.

Anal. Calcd. for $C_{26}H_{32}N_4O_2 \cdot 0.75$ cyclohexane: C, 73.9; H, 8.34; N, 11.3. Found: C, 73.75; H, 8.36; N, 10.79%.

NMR (300 MHz, DMSO) δ: 8.8 (d, J=7.5 Hz, 1H), 7.3–7.65 (m, 9H), 4.95 (d, J=7Hz,1H), 3.57 (½AB, J=13 Hz, 1H), 3.48 (½AB, J=13 Hz, 1H), 3.1–3.4 (m, 1H), 3.27 (s, 3H), 2.65 (s, 3H), 0.9–1.9 (m, 10H).

By substituting the appropriate acid for phenylpropionic acid, and employing the procedures substantially as described in Example 1 the following compounds were prepared.

EXAMPLE 7

(±)-N-[2,3-Dihydro-1-methyl-2-oxo-5-(N-cyclohexyl-N-methylamino)-1H-1,4-benzo-diazepin-3-yl]-2-cyclohexylacetamide m.p. 158°–159° C.

Anal. Calcd. for $C_{25}H_{36}N_4O_2$ 0.85 cyclohexane: C, 72.86; H, 9.39; N, 11.29. Found: C, 72.46; H, 9.4; N, 10.9%.

NMR (300 MHz, DMSO) δ: 8.44 (d, J=7.8 Hz, 1H), 7.5–7.65 (m, 2H), 7.46 (dd, J=7.8, 1.2 Hz, 1H), 7.32 (m, 1H), 4.95 (d, J=8 Hz, 1H), 3.15–3.45 (m, 1H), 3.26 (s, 3H), 2.64 (s, 3H), 1.95–2.1 (m, 2H), 0.8–1.9 (m, 21H).

EXAMPLE 8

N-[2,3-Dihydro-1-methyl-2-oxo-5-(N-cyclohexyl-N-methylamino)-1H-1,4-benzo-diazepin-3-yl]-4-phenylbutanamide m.p. 140°–141° C.

Anal. Calcd. for $C_{27}H_{34}N_4O_2$ 0.7 Water: C, 70.62; H, 7.77; N, 12.2. Found: C, 70.58; H, 7.54; N, 12.11%.

NMR (300 MHz, DMSO) δ: 8.52 (d, J=8.1 Hz, 1H), 7.1–7.6 (m, 9H), 4.97 (d, J=9.1 Hz, 1H), 3.1–3.45 (m, 1H), 3.26 (s, 3H), 2.64 (s, 3H), 2.52 (m, 2H), 2.10–2.30 (m, 2H), 0.9–1.9 (m, 12H).

EXAMPLE 9

(±)-N-[2,3-Dihydro-1-methyl-2-oxo-5-(N-cyclohexyl-N-methylamino)-1H-1,4-benzo-diazepin-3-yl]-3-cyclohexylpropanamide m.p. 170°–171° C.

Anal. Calcd. for $C_{26}H_{38}N_4O_2$ 0.55 EtOAc 0.5 cyclohexane: C, 70.81; H, 9.22; N, 10.59. Found: C, 70.88; H, 9.2; N, 10.55%.

NMR (300 MHz, DMSO) δ: 8.46 (d, J=8.1 Hz, 1H), 7.28–7.65 (m, 4H), 4.95 (d, J=8.1 Hz, 1H), 3.1–3.4 (m, 1H), 3.26 (s, 3H), 2.64 (s, 3H), 2.17 (t, J=7.1 Hz, 2H), 0.7–1.9 (m, 23H).

EXAMPLE 10

(±)-N-[2,3-Dihydro-1-methyl-2-oxo-5-(N,N-diethylamino)-1H-1,4-benzodiazepin-3-yl]-5-phenylpentanamide m.p. 134°–135° C.

Anal. Calcd. for $C_{25}H_{32}N_4O_2$, 0.25$H_2O$: C, 70.64; H, 7.71; N, 13.18. Found: C, 70.7; H, 7.94; N, 13.16%.

NMR (300 MHz, DMSO) δ: 8.48 (d, J=8.1 Hz, 1H), 7.1–7.6 (m, 9H), 4.97 (d, J=8.1 Hz, 1H), 3.25–3.4 (m, 2H), 3.27 (s, 3H), 2.95–3.1 (m, 2H), 2.53 (t, J=7.1 Hz, 2H), 2.20 (t, J=7.1 Hz, 2H), 1.4–1.6 (m, 4H), 0.97 (t, J=7.1 Hz, 6H).

EXAMPLE 11

(±)-N-[2,3-Dihydro-1-methyl-2-ox o-5-(N,N-diethylamino)-1H-1,4-benzodiazepin-3-yl]-2-cyclohexylacetamide m.p. 192°–193 ° C.

Anal. Calcd. for $C_{22}H_{32}N_4O_2$, 0.9$H_2O$: C, 65.93; H, 8.5; N, 13.98. Found: C, 65.91; H, 7.9; N, 14.05%.

NMR (300 MHz, DMSO) δ: 8.43 (d, J=8.1 Hz, 1H), 7.2–7.65 (m, 4H), 4.96 (d, J=8.1 Hz, 1H), 3.2–3.3 (m, 2H), 3.27 (s, 3H), 2.9–3.1 (m, 2H), 1.95–2.1 (m, 2H), 0.8–1.7 (m, 17H).

EXAMPLE 12

(±)-N-[2,3-Dihydro-1-methyl-2-oxo-5-(N,N-diethylamino)-1H-1,4-benzodiazepin-3-yl]-3-cyclohexylpropanamide m.p. 209°–210° C.

Anal. Calcd. for $C_{23}H_{34}N_4O_2$: C, 69.31; H, 8.6; N, 14,06. Found: C, 69.38; H, 8.69; N, 13.69%.

NMR (300 MHz, DMSO) δ: 8.45 (d, J=8.1 Hz, 1H), 7.2–7.65 (m, 4H), 4.96 (d, J=8.1 Hz, 1H), 3.2–3.4 (m, 2H), 3.27 (s, 3H), 2.9–3.1 (m, 2H), 2.17 (t, J=7.3 Hz, 2H), 0.7–1.7 (m, 19H).

By using hexahydroazepine in place of N-methylcyclohexylamine, and the appropriate acid the following compounds were prepared using the processes substantially as described in Example 1.

EXAMPLE 13

N-[2,3-Dihydro-1-methyl-2-oxo-5-(hexahydroazepin-1-yl)-1H-1,4-benzodiazepin-3-yl]-2-cyclohexyl acetamide m.p. 205°–207° C.

Anal. Calcd. for $C_{24}H_{34}N_4O_2$. 0.25$H_2O$ C, 70.21; H, 8.35; N, 13.65. Found: C, 69.44; H, 8.38; N, 13.50%.

NMR (300 MHz, $CD_3OD$) δ 0.95–2.83 (m, 19H), 2.08 (m, 2H), 3.41 (m, 4H), 4.94 (s, 3H), 5.09 (d, 1H), 7.29–7.63 (m, 4H).

EXAMPLE 14

(±)-3-cyclohexyl-N-[2,3-Dihydro-1-methyl-2-oxo-5-(hexahydroazepin-1-yl)-1H1,4-benzodiazepin-3-yl]propanamide m.p. 100°–102° C.

Anal. Calcd. for $C_{25}H_{36}N_4O_2$.HCl, 0.50$H_2O$; 0.30 EtOAc: C, 63.38; H, 8.2; N, 11.28. Found: C, 63.36; H, 8.09; N, 11.3%.

δ: 8.54 (d, J=9.0 Hz, 1H), 7.79–7.74 (m, 1H), 7.54 (d, J=7.8 Hz, 1H), 7.49–7.40 (m, 2H), 5.69 (dd, J=9.0, 5.6 Hz, 2H), 4.55–4.4 (m, 1H), 4.20–4.00 (m, 1H), 3.54–3.49 (m, 2H), 3.46 (s, 3H), 2.47–2.41 (m, 2H), 2.09–1.97 (m, 5H), 1.82–1.51 (m, 10H), 1.28–1.12 (m, 4H), 0.93–0.85 (m, 2H).

By using N-methylbenzylamine in place of N-methylcyclohexylamine, and the appropriate acid, the following compounds were prepared using the processes substantially as described in Example 1.

EXAMPLE 15

N-[2,3-Dihydro-1-methyl-2-oxo-5-(N,N-dimethylamino)-1H-1,4-benzodiazepin-3-yl]-3-cyclohexylpropanamide m.p. 197.5°–198° C.

Anal. Calcd. for $C_{21}H_{30}N_4O_2$.0.05 C, 68.08; H, 8.16; N, 15.12. Found: C, 67.91; H, 8.17; N, 14.95%.

NMR (300 MHz, $CDCl_3$) δ 0.81–1.77 (m, 13H), 2.30 (m, 2H), 2.86 (s, 6H), 3.21 (s, 3H), 5.26 (d, 1H), 6.99 (d, 1H), 7.22–7.52 (m, 4H)

2,3-Dihydro-1-benzyl-2-oxo-1H-1,4-benzodiazepine-2,5-dione was prepared from N-benzylisatoic anhydride (Transworld Chemicals) and glycine using the method described by Bock et al J. Org. Chem. 52, 1644, (1987). This was then reacted with dimethylamine in place of the N-methyl cyclohexylamine, and the appropriate acid substantially as described above in Example 1 to give the following compounds:

EXAMPLE 16

N-[2,3-Dihydro-1-propyl-2-oxo-5-(N,N-dimethylamino)-1H-1,4-benzodiazepin-3-yl]-2-cyclohexylacetanide m.p. 196°–197° C.

Anal. Calcd. for $C_{22}H_{32}N_4O_2$: C, 68.72; H, 8.39; N, 14.57. Found: C, 68.54; H, 8.31; N, 14.44%.

NMR (300 MHz, DMSO) δ: 0.59–2.12 (m, 16H), 2.78 (m, 2H), 3.32 (5, 6H), 3.58 (m, 1H), 4.19 (m, 1H), 4.95 (d, 1H), 7.30–7.62 (m, 4H), 8.46 (d, 1H).

Additional compounds which can be used to selectively blockade the IKs channel also include for example:

EXAMPLE 17

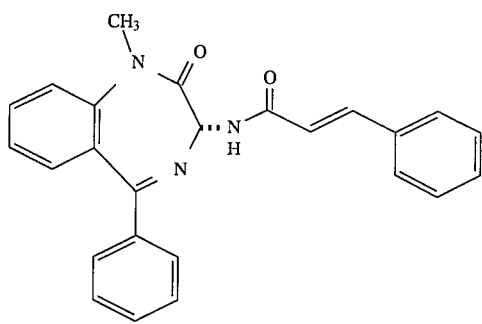

(3R)

(E)-(+)-N-[(3R)-2,3-Dihydro-1-methyl-2-oxo-5-phenyl-1H-1,4-benzodiazepin-3-yl]-3-phenyl-2-propenamide A solution of (E)-3-phenyl-2-propenoyl chloride (367 mg, 2.2 mmol) in methylene chloride (1 mL) was added to a solution of 3(R)-amino-1,3-dihydro-1-methyl-5-phenyl-2H-1,4-benzodiazepin-2-one (J. Org. Chem. 1987, 52, 3232–3239) (531 mg, 2.0 mmol) and triethylamine (307 μL, 225 mg, 2.2 mmol) in methylene chloride (10 mL). The mixture was stirred at room temperature for 25 min. and the solvent was evaporated under reduced pressure. The residue was purified by flash column chromatography on silica gel, eluting with $CH_2Cl_2/Et_2O$ (95:5) and the residue was triturated with $Et_2O$. The solid was collected and dried in vacuo at 70° C. to give (E)-(+)-N-[(3R)-2,3-dihydro-1-methyl-2-oxo-5-phenyl-1H-1,4-benzodiazepin-3-yl]-3-phenyl-2-propenamide as a colorless solid (170 mg, 21%), m.p. 140°–142° C., $[α]_D$+86.7° (c=0.173, $CH_2Cl_2$).

$δ_H$ (CDCl$_3$) 7.70–7.26 (16H, m), 6.63 (1H, d, J15.6 Hz), 5.68 (1H, d, J 8.3 Hz), and 3.50 (3H, s).

Anal. Calcd. for $C_{25}H_{21}N_3O_2.0.15$ $(C_2H_5)_2O$: C, 75.63; H, 5.58; N, 10.33. Found: C, 75.29; H, 5.57; N, 10.33%.

Employing the procedure substantially as described above, but substituting an appropriate acid chloride for the (E)-3-phenyl-2-propenoyl chloride, the following compounds were prepared:

EXAMPLE 18

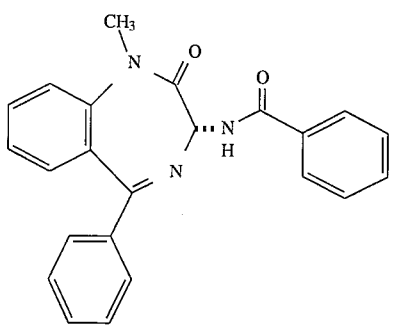

(+)-N-[(3R)-2,3-Dihydro-1-methyl-2-oxo-5-phenyl-1H-1,4-benzo-diazepin-3-yl]benzamide m.p. 224°–225° C., $[α]_D$+89.2° (c=0.141, $CH_2Cl_2$).

$δ_H$ (CDCl$_3$) 8.04 (1H, d, J 8.1 Hz), 7.96 (2H, d, J 6.8 Hz), 7.64–7.36 (10H, m), 7.27 (2H, t, J 7.6 Hz), 5.74 (1H, d, J 7.8 Hz), and 3.51 (3H, s).

Anal. Calcd. for $C_{23}H_{19}N_3O_2.0.20H_2O$: C, 74.06; H, 5.24; N, 11.26. Found: C, 74.13; H, 5.12; N, 11.16%.

EXAMPLE 19

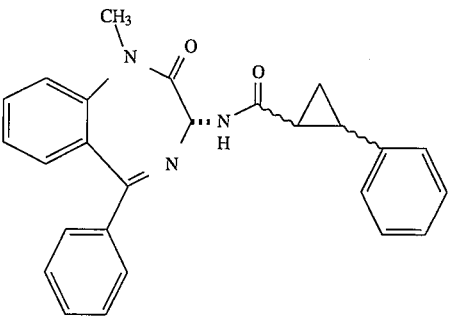

First diastereoisomer to elute:

(−)-N-[(3R )-2,3-Dihydro-1-methyl-2-oxo-5-phenyl-1H-1,4-benzo-diazepin-3-yl](trans-2-phenyl-1-cyclopropane)carboxamide m.p. 180°–181° C., $[α]_D$–155.8° (c=0.434, $CH_2Cl_2$).

$δ_H$ (CDCl$_3$) 7.62–7.09 (15H, m), 5.59 (1H, d, J 8.1 Hz), 3.47 (3H, s), 2.52–2.45 (1H, m), 1.90–1.84 (1H, m),1.69–1.56 (1H, m), and 1.38–1.32 (1H, m).

Anal. Calcd. for $C_{26}H_{23}N_3O_2.0.25H_2O$: C, 75.43; H, 5.72; N, 10.15. Found: C, 75.38; H, 5.64; N, 9.94%.

Second diastereoisomer to elute:

(+)-N-[(3R)-2,3-Dihydro-1-methyl-2-oxo-5-phenyl-1H-1,4-benzo-diazepin-3-yl](trans-2-phenyl-1-cyclopropane)carboxamide m.p. 104°–107° C., $[α]_D$+328.2° (c=0.098, $CH_2Cl_2$).

$δ_H$ (CDCl$_3$) 7.62–7.13 (15H, m), 5.60 (1H, d, J 8.3 Hz), 3.48 (3H, s), 2.59–2.54 (1H, m), 1.93–1.87 (1H, m),1.62–1.56 (1H, m, overlaps with water), and 1.33–1.25 (1H, m).

Anal. Calcd. for $C_{26}H_{23}N_3O_2.0.50H_2O.0.45PhCH_3$: C, 76.13; H, 5.95; N, 9.14. Found: C, 76.10; H, 5.94; N, 9.17%.

EXAMPLE 20

(+)-N-[(3R)-2,3-Dihydro-1-methyl-2-oxo-5-phenyl-1H-1,4-benzodiazepin-3-yl]-1H-indole-2-carboxamide m.p. 167°–177° C., $[α]_D$+113° (c=1.103, $CH_2Cl_2$).

$\delta_H$ (CDCl$_3$) 9.15 (1H, br s), 8.10 (1H, d, J 9.0 Hz), 7.75–7.10 (14H, m), 5.75 (1H, d, J 9.0 Hz), and 3.50 (3H, s).

Anal. Calcd. for C$_{25}$H$_{20}$N$_4$O$_2$: C, 73.51; H, 4.94; N, 13.72. Found: C, 73.31; H, 4.80; N, 13.62%.

EXAMPLE 21

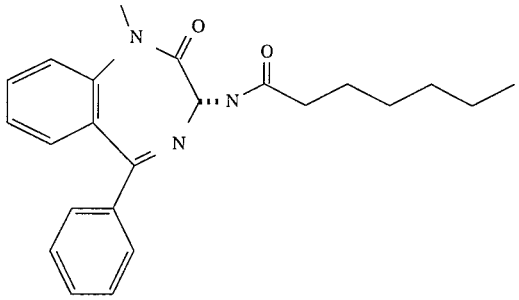

(+)-N-[(3R)-2,3-Dihydro-1-methyl-2-oxo-5-phenyl-1H-1,4-benzo-diazepin-3-yl]heptanamide m.p. 49°–54° C., [α]$_D$+69.5° (c=1.000, MeOH).

Anal. Calcd. for C$_{23}$H$_{27}$N$_3$O$_2$.0.40H$_2$O: C, 71.81; H, 7.28; N, 10.92. Found: C, 71.90; H, 7.09; N, 10.85%.

EXAMPLE 22

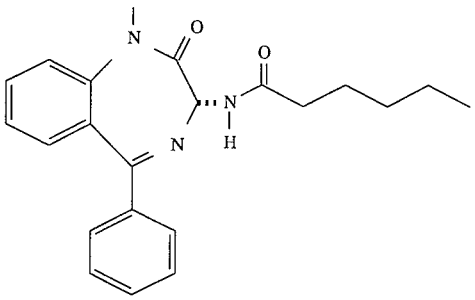

(+)-N-[(3R)-2,3-Dihydro-1-methyl-2-oxo-5-phenyl-1H-1,4-benzo-diazepin-3-yl]hexanamide

[α]$_D$+72.6° (c=0.920, MeOH).

Anal. Calcd. for C$_{22}$H$_{25}$N$_3$O$_2$: C, 72.70; H, 6.93; N, 11.56. Found: C, 72.44; H, 6.75; N, 11.25%.

EXAMPLE 23

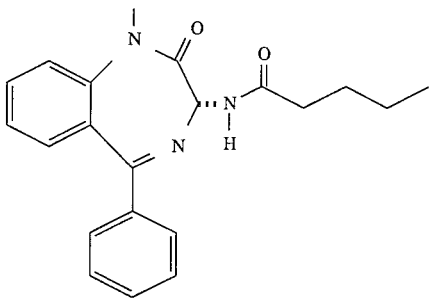

(+)-N-[(3R)-2,3-Dihydro-1-methyl-2-oxo-5-phenyl-1H-1,4-benzo-diazepin-3-yl]pentanamide

[α]$_D$+68.2° (c=1.310, MeOH).

Anal. Calcd. for C$_{21}$H$_{23}$N$_3$O$_2$.0.25CHCl$_3$: C, 68.21; H, 6.26; N, 11.26. Found: C, 68.2; H, 6.29; N, 11.17%.

EXAMPLE 24

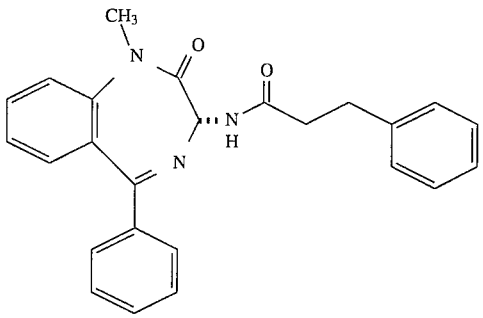

(+)-N-[(3R)-2,3-Dihydro-1-methyl-2-oxo-5-phenyl-1H-1,4-benzo-diazepin-3-yl]-3-phenylpropanamide Oxalyl chloride (158 μL, 230 mg, 1.81 mmol) was added to a mixture of 3-phenylpropanoic acid (249 mg, 1.66 mmol) and DMF (1 drop) in THF (10 mL) and the mixture was stirred at room temperature for 40 min. 3(R)-Amino-1,3-dihydro-1-methyl-5-phenyl-2H-1,4-benzodiazepin-2-one (J. Org. Chem. 1987, 52, 3232–3239) (400 mg, 1.51 mmol) and triethylamine (252 μL, 183 mg, 1.81 mmol) were added and the mixture was stirred at room temperature for 18 h. The mixture was poured into saturated aqueous sodium hydrogen carbonate (20 mL) and extracted with ethyl acetate (3×20 mL). The combined organic fractions were dried (Na$_2$SO$_4$) and the solvent was evaporated under reduced pressure. The residue was purified by flash column chromatography on silica gel, eluting with CH$_2$Cl$_2$/Et$_2$O (95:5) and the residue was recrystallized from toluene/hexane to give (+)-N-[(3R)-2,3-dihydro-1-methyl-2-oxo-5-phenyl-1H-1,4-benzodiazepin-3-yl]-3-phenylpropanamide as a colorless solid (380 mg, 63%), m.p. 179° C., [α]$_D$+100.4° (c=0.225, CH$_2$Cl$_2$).

$\delta_H$ (CDCl$_3$) 7.62–7.57 (2H, m), 7.47–7.21 (13H, m), 5.54 (1H, d, J 8.1 Hz), 3.47 (3H, s), 3.03 (2H, t, J 7.8 Hz), and 2.73–2.67 (2H, m).

Anal. Calcd. for C$_{25}$H$_{23}$N$_3$O$_2$.0.15H$_2$O:

C, 75.04; H, 5.87; N, 10.50. Found: C, 75.06; H, 5.78; N, 10.55%.

Employing the procedure substantially as described above, but substituting an appropriate carboxylic acid for the 3-phenyl-propanoic acid, the following compounds were prepared:

EXAMPLE 25

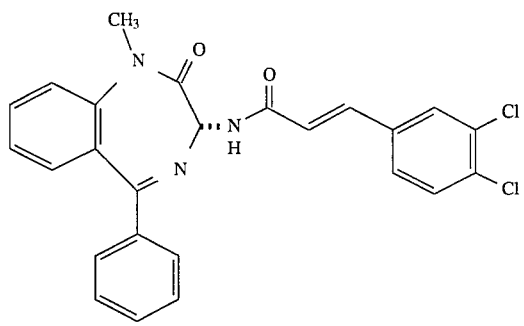

E-(+)-N-[(3R)-2,3-Dihydro-1-methyl-2-oxo-5-phenyl-1H-1,4-benzodiazepin-3-yl]-3-(3,4-dichlorophenyl)-2-propenamide m.p. 145°–147° C., [α]$_D$+77.8° (c=0.126, CH$_2$Cl$_2$).

δ$_H$ (CDCl$_3$) 7.64–7.25 (14H, m), 6.61 (1H, d, J 15.6 Hz), 5.65 (1H, d, J 8.0 Hz), and 3.50 (3H, s).

Anal. Calcd. for C$_{25}$H$_{19}$N$_3$O$_2$Cl$_2$: C, 64.67; H, 4.12; N, 9.05. Found: C, 64.57; H, 4.25; N, 9.01%.

EXAMPLE 26

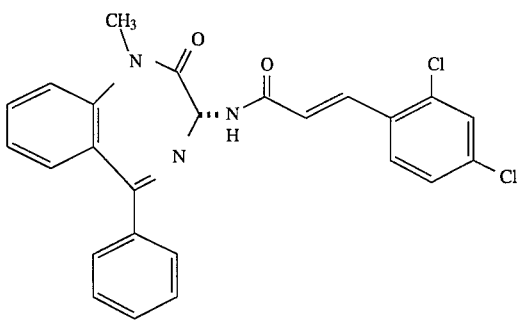

E-(+)-N-[(3R)-2,3-Dihydro-1-methyl-2-oxo-5-phenyl-1H-1,4-benzodiazepin-3-yl]-3-(2,4-dichlorophenyl)-2-propenamide m.p. 137°–139° C., [α]$_D$+66.0° (c=0.144, CH$_2$Cl$_2$).

δ$_H$ (CDCl$_3$) 8.02 (1H, d, J 15.6 Hz), 7.73–7.26 (13H, m), 6.66 (1H, d, J 15.6 Hz), 5.81 (1H, d, J 8.8 Hz), and 3.53 (3H, s).

Anal. Calcd. for C$_{25}$H$_{19}$Cl$_2$N$_3$O$_2$: C, 64.67; H, 4.12; N, 9.05. Found: C, 64.28; H, 4.24; N, 8.83%.

EXAMPLE 27

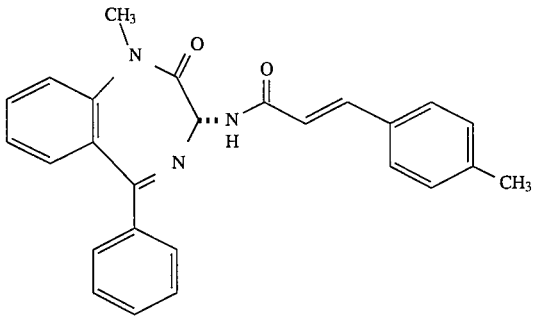

E-(+)-N-[(3R)-2,3-Dihydro-1-methyl-2-oxo-5-phenyl-1H-1,4-benzodiazepin-3-yl]-3-(4-methylphenyl)-2-propenamide m.p. 133°–135° C., [α]$_D$+90.4° (c=0.125, CH$_2$Cl$_2$).

δ$_H$ (CDCl$_3$) 7.68–7.19 (15H, m), 6.59 (1H, d, J 15.6 Hz), 5.70 (1H, d, J 8.0 Hz), 3.50 (3H, s), and 2.38 (3H, s).

Anal. Calcd. for C$_{26}$H$_{23}$N$_3$O$_2$: C, 76.26; H, 5.66; N, 10.26. FOUND: C, 75.93; H, 5.82; N, 10.10%.

EXAMPLE 28

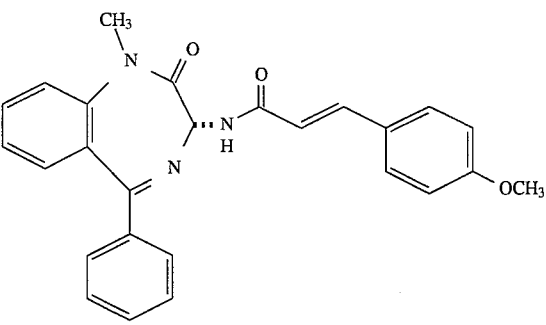

E-(+)-N-[(3R)-2,3-Dihydro-1-methyl-2-oxo-5-phenyl-1H-1,4-benzodiazepin-3-yl]-3-(4-methoxyphenyl)-2-propenamide m.p. 129°–133° C., [α]$_D$+89.9° (c 0.188, CH$_2$Cl$_2$).

δ$_H$ (CDCl$_3$) 7.65–7.24 (14H, m), 6.92 (1H, d, J 8.8 Hz), 6.50 (1H, d, J 15.6 Hz), 5.69 (1H, d, J 8.0 Hz), 3.84 (3H, s), and 3.50 (3H, s).

Anal. Calcd. for C$_{26}$H$_{23}$N$_3$O$_3$.0.30H$_2$O: C, 72.48; H, 5.52; N, 9.75. Found: C, 72.75; H, 5.60; N, 9.36%.

EXAMPLE 29

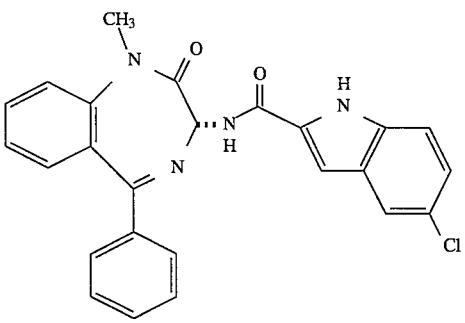

(+)-5-Chloro-N-[(3R)-2,3-dihydro-1-methyl-2-oxo-5-phenyl-1H-1,4-benzodiazepin-3-yl]indole-2-carboxamide m.p. 160°–164° C., [α]$_D$+103.8° (c =0.160, CH$_2$Cl$_2$).

δ$_H$ (CDCl$_3$) 9.71 (1H, br s), 8.13 (1H, d, J 7.8 Hz), 7.68–7.09 (13H, m), 5.75 (1H, d, J 7.8 Hz), and 3.53 (3H, s).

Anal. Calcd. for C$_{25}$H$_{19}$ClN$_4$O$_2$.0.25H$_2$O.0.15PhCH$_3$: C, 67.84; H, 4.49; N, 12.15. Found: C, 67.80; H, 4.41; N, 12.07%.

EXAMPLE 30

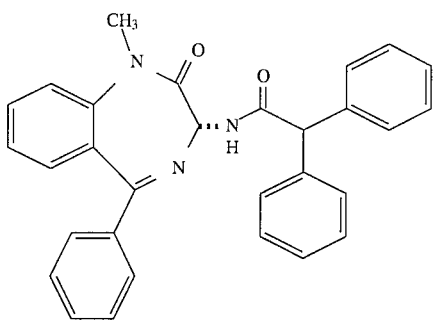

(+)-N-[(3R)-2,3-Dihydro-1-methyl-2-oxo-5-phenyl-
1H-1,4-benzo-diazepin-3-yl]-2,2-diphenyl-
ethanamide m.p. 200°–201° C., $[\alpha]_D$+97.0° (c=0.168, CH$_2$Cl$_2$).

$\delta_H$ (CDCl$_3$) 7.60–7.22 (20H, m), 5.58 (1H, d, J 8.1 Hz), 5.08 (1H, s), and 3.44 (3H, s).

Anal. Calcd. for C$_{30}$H$_{25}$N$_3$O$_2$.0.15PhCH$_3$: C, 78.79; H, 5.55; N, 8.88. Found: C, 78.81; H, 5.63; N, 9.07%.

EXAMPLE 31

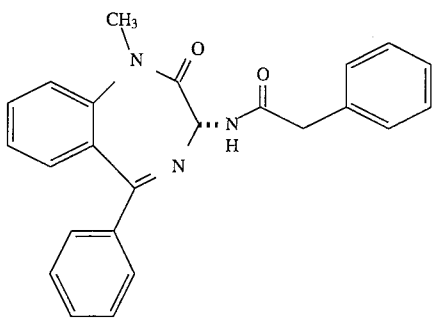

(+)-N-[(3R)-2,3-Dihydro-1-methyl-2-oxo-5-phenyl-
1H-1,4-benzo-diazepin-3-yl]-2-phenylethanamide m.p. 241°–242° C. (dec.), $[\alpha]_D$+85.5° (c =0.159, CH$_2$Cl$_2$).

$\delta_H$ (CDCl$_3$) 7.59–7.55 (3H, m), 7.46–7.22 (12H, m), 5.51 (1H, d, J 8.1 Hz), 3.72 (2H, s), and 3.44 (3H, s).

Anal. Calcd. for C$_{24}$H$_{21}$N$_3$O$_2$.0.55H$_2$O: C, 73.28; H, 5.66; N, 10.68. Found: C, 73.25; H, 5.38; N, 10.47%.

EXAMPLE 32

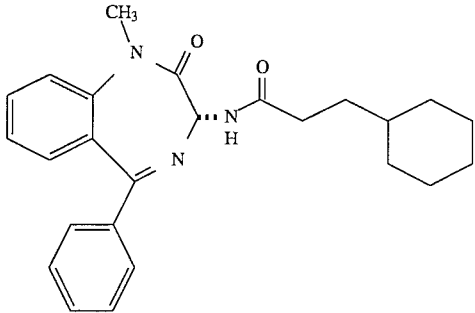

(+)-3-Cyclohexyl-N-[(3R)-2,3-dihydro-1-methyl-2-
oxo-5-phenyl-1H-benzodiazepin-3-yl]propanamide m.p. 144.5°–145.5° C., $[\alpha]_D$+83.1° (c=0.116, CH$_2$Cl$_2$).

$\delta_H$ (CDCl$_3$) 7.62–7.56 (3H, m), 7.46–7.21 (7H, m), 5.55 (1H, d, J 8.3 Hz), 3.48 (3H, s), 2.41–2.36 (2H, m), 1.77–1.58 (7H, m), 1.31–1.16 (4H, m), and 0.98–0.90 (2H, m).

Anal. Calcd. for C$_{25}$H$_{29}$N$_3$O$_2$: C, 74.41; H, 7.24; N, 10.41. Found: C, 74.46; H, 7.27; N, 10.58%.

EXAMPLE 33

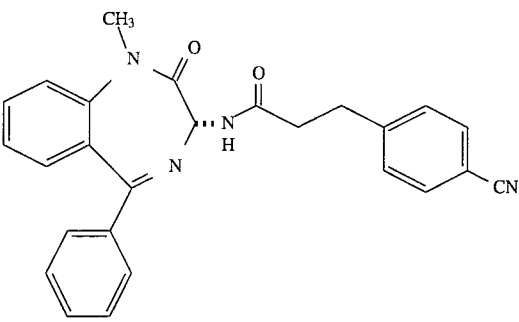

(+)-N-[(3R)-2,3-Dihydro-1-methyl-2-oxo-5-phenyl-1H-1,4-
benzo-diazepin3-yl]-3-(4-cyanophenyl)propanamide m.p. 81°–85° C., $[\alpha]_D$+91.0° (c=0.111, CH$_2$Cl$_2$).

$\delta_H$ (CDCl$_3$) 7.64–7.55 (4H, m), 7.48–7.16 (10H, m), 5.50 (1H, d, J 8.3 Hz), 3.47 (3H, s), 3.08 (2H, t, J 7.6 Hz), and 2.74–2.69 (2H, m).

Anal. Calcd. for C$_{26}$H$_{22}$N$_4$O$_2$.0.60H$_2$O.0.50PhCH$_3$: C, 73.93; H, 5.62; N, 11.69. Found: C, 73.98; H, 5.61; N, 11.71%.

EXAMPLE 34

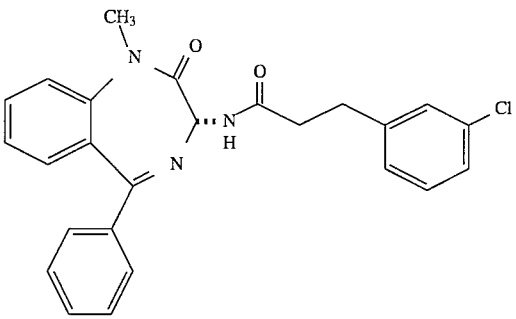

(+)-N-[(3R)-2,3-Dihydro-1-methyl-2-oxo-5-phenyl-1H-1,4-
benzo-diazepin-3-yl]-
3-(3-chlorophenyl)propanamide m.p. 157°–159° C., $[\alpha]_D$+90.7° (c=0.134, CH$_2$Cl$_2$).

$\delta_H$ (CDCl$_3$) 7.62–7.57 (3H, m), 7.47–7.12 (1 1H, m), 5.53 (1H, d, J 8.1 Hz), 3.47 (3H, s), 3.00 (2H, t, J 7.3 Hz), and 2.71–2.66 (2H, m).

Anal. Calcd. for C$_{25}$H$_{22}$ClN$_3$O$_2$.0.55H$_2$O: C, 67.96; H, 5.27; N, 9.51. Found: C, 67.99; H, 5.18; N, 9.26%.

EXAMPLE 35

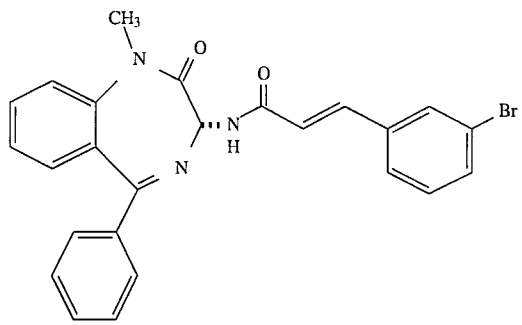

E-(+)-N-[(3R)-2,3-Dihydro-1-methyl-2-oxo-5-phenyl-1H-1,4-benzodiazepin-3-yl]-3-(3-bromophenyl)-2-propenamide m.p. 221°–223 d° C, $[\alpha]_D$+65.5° (c=0.206, CH$_2$Cl$_2$).

$\delta_H$ (CDCl$_3$) 7.69 (1H, br s), 7.64–7.57 (4H, m), 7.51–7.37 (6H, m), 7.29–7.19 (4H, m), 6.62 (1H, d, J 15.6 Hz), 5.66 (1H, d, J 8.1 Hz), and 3.50 (3H, s).

Anal. Calcd. for C$_{25}$H$_{20}$BrN$_3$O$_2$.0.35H$_2$O.0.20PhCH$_3$: C, 63.54; H, 4.46; N, 8.42. Found: C, 63.50; H, 4.39; N, 8.42%.

EXAMPLE 36

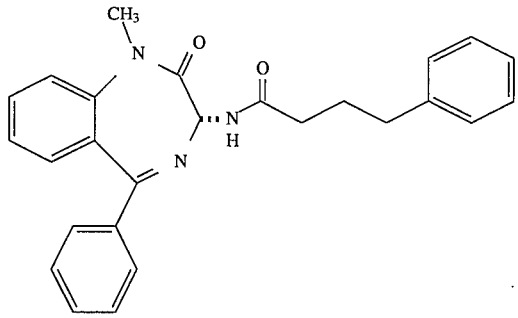

(+)-N-[(3R)-2,3-Dihydro-1-methyl-2-oxo-5-phenyl-1H-1,4-benzo-diazepin3-yl]-4-phenylbutanamide m.p. 65°–74° C., $[\alpha]_D$+77.4° (c=0.155, CH$_2$Cl$_2$).

$\delta_H$ (CDCl$_3$) 7.62–7.56 (3H, m), 7.46–7.19 (12H, m), 5.55 (1H, d, J 8.1 Hz) 3.47 (3H, s), 2.71 (2H, t, J 7.6 Hz), 2.42–2.37 (2H, m), and 2.09–2.01 (2H, m).

Anal. Calcd. for C$_{26}$H$_{25}$N$_3$O$_2$.0.30H$_2$O: C, 74.91; H, 6.19; N, 10.08. Found: C, 74.93; H, 6.05; N, 10.07%.

EXAMPLE 37

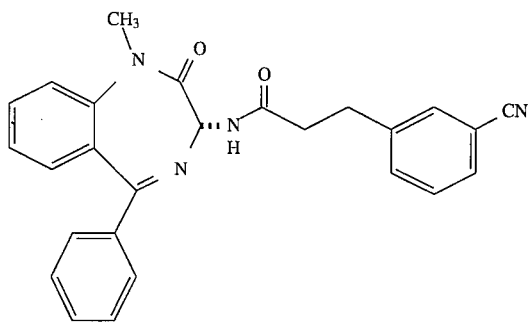

(+)-N-[(3R)-2,3-Dihydro-1-methyl-2-oxo-5-phenyl-1H-1,4-benzo-diazepin-3-yl]-3-(3-cyanophenyl)-propanamide m.p. 110°–112° C., $[\alpha]_D$+84.2° (c=0.202, CH$_2$Cl$_2$).

$\delta_H$ (CDCl$_3$) 7.63–7.22 (14H, m), 5.51 (1H, d, J 8.1 Hz), 3.47 (3H, s), 3.06 (2H, t, J 7.8 Hz), and 2.74–2.68 (2H, m).

Anal. Calcd. for C$_{26}$H$_{22}$N$_4$O$_2$.0.50H$_2$O: C, 72.37; H, 5.37; N, 12.98. Found: C, 72.52; H, 5.12; N, 12.59%.

EXAMPLE 38

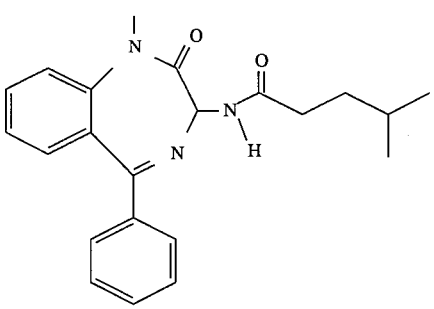

(+)-N-[(3R)-2,3-Dihydro-1-methyl-2-oxo-5-phenyl-1H-1,4-benzo-diazepin-3-yl]-4-methylpentanamide m.p. 123°–125° C., $[\alpha]_D$+66.8° (c=0.500, MeOH).

Anal. Calcd. for C$_{22}$H$_{25}$N$_3$O$_2$.0.45H$_2$O: C, 71.12; H, 7.03; N, 11.31. Found: C, 71.08; H, 6.81; N, 11.42%.

EXAMPLE 39

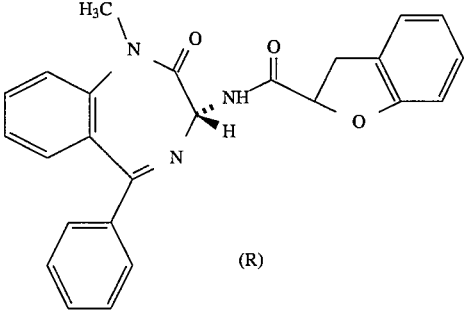

(+)-N-[(3R)-2,3-Dihydro-1-methyl-2-oxo-5-phenyl-1H-1,4-benzo-diazepin-3-yl]-2,3-dihydro-benzofuran-2-carboxamide Diisopropylethylamine (0.3 mL, 223 mg, 1.72 mmol) was added to a stirred, cooled (0 °C.) solution of 3(R)-amino-1,3-dihydro-1-methyl-5-phenyl-2H-1,4-benzodiazepin-2-one (J. Org. Chem. 1987, 52, 2–3239) (400 mg, 1.5 mmol), 2,3-dihydrobenzofuran-2-carboxylic acid (274 mg, 1.7 mmol), 1-(3-dimethylaminopropyl)-3-ethylcarbodi-imide hydrochloride (583 mg, 3.0 mmol), and 1-hydroxybenzotriazole (479 mg, 3.1 mmol) in DMF (4.5 mL). The mixture was stirred at room temperature for 18 h., poured into aqueous hydrochloric acid (3M, 12 mL) and extracted with ethyl acetate (3×20 mL). The combined organic fractions were washed with saturated aqueous sodium hydrogen carbonate (20 mL) and brine (20 mL), dried (MgSO$_4$) and evaporated under reduced pressure. The residue was crystallized from 2-chloro-2-methylpropane/hexane to give (+)-N-[(3R)-2,3-dihydro-1-methyl-2-oxo-5-phenyl-1H-1,4-benzodiazepin-3-yl]-2,3-dihydrobenzofuran-2-carboxamide as a colorless solid (156 mg, 25%), m.p. 141°–180° C., [α]$_D$+ 127.1° (c=0.425, CHCl$_3$).

δ$_H$ (CDCl$_3$) (3:1 Mixture of diastereoisomers) 8.44 (1H, m), 7.65–6.91 (13H, m), 5.52 (1H, m), 5.28 (1H, m), and 3.70–3.40 (5H, m).

Anal. Calcd. for C$_{25}$H$_{21}$ N$_3$O$_3$·0.25 Hexane C, 73.50; H, 5.70; N, 9.71. Found: C, 74.12; H, 5.57; N, 9.71%.

EXAMPLE 40

Although not a pure IKs inhibitor, the synthesis of (+)-N-[(3R)-2,3-dihydro-1-methyl-2-oxo-5-phenyl-1H-1,4-benzo-diazepin-3-yl]-1'-(1,1-dimethylethoxycarbonyl)spiro(cyclohexan-4,4'-piperidine)-1-carboxamide illustrates a procedure for preparing other compounds which are active.

Step A:

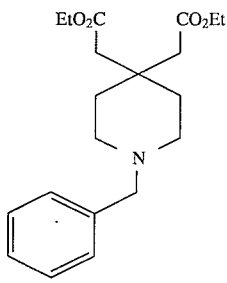

Diethyl 1-benzylpiperidine-4,4-diacetate

Ethanol (120 mL) was cooled in ice and ammonia bubbled through to give a saturated solution. 1-Benzyl-4-piperidone (40.0 g, 211 mmol) and ethyl cyanoacetate (47.8 g, 423 mmol) were added, the reaction vessel stoppered and stored at 0° C. overnight. The solid was collected, washed with ethanol and ether and dried in vacuo to give a yellow solid (68.86 g). The solid (58.86 g) was dissolved in a mixture of sulfuric acid (70 mL, 98%) and water (60 mL) and heated under reflux for three days the mixture cooled and most of the water evaporated. The residue was azeotroped with ethanol (4×750 mL), further ethanol (500 mL) added and the mixture heated under reflux for 20 h, cooled in ice and sodium carbonate (100 g) added slowly with vigorous stirring. The ethanol was evaporated under reduced pressure, water (800 mL) added and the mixture extracted with methylene chloride (3×400 mL). The combined organic extracts were dried (Na$_2$SO$_4$) and the solvent evaporated to give Diethyl 1-benzylpiperidine-4,4-diacetate (37.51 g). A small portion of this was purified by flash column chromatography.

NMR (300 MHz, CDCl$_3$) δ: 7.2–7.4 (m, 5H), 4.11 (q, J=7.3 Hz,4H), 3.50 (s, 2H), 2.56 (s, 4H), 2.4 (m, 4H), 1.7 (m, 4H), 1.24 (t, J=7.3 Hz, 6H).

Step B:

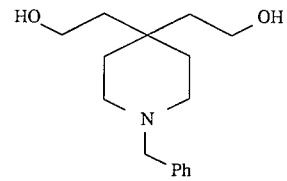

1-Benzylpiperidine-4,4-diethanol

A solution of the diester (12.2 g, 35 mmol) in ether (25 mL) was added to a cooled (−30° C.) and stirred suspension of LiAlH$_4$ (2.1 g, 55 mmol) in ether (400 mL), under argon. THF (60 mL) was added and the reaction mixture allowed to warm to room temperature. After recooling to 0° C., water (2.2 mL), 1M NaOH (4.4 mL) and water (5 mL) were added, the reaction mixture stirred vigorously for 30 min and the solid filtered off, washing well with ether. The combined filtrates were evaporated to afford a white solid which was tritutrated with ether to give 8 g of 1-benzylpiperidine-4,4-diethanol.

m.p. 75°–78° C.

NMR (300 MHz, CDCl$_3$) δ: 7.2–7.4 (m, 5H), 3.7 (t, J=6.8 Hz, 4H), 3.52 (s, 2H), 2.7 (brs, 2H), 2.43 (m, 4H), 1.66 (t, J=6.8 Hz, 4H), 1.5 (m, 4H).

Step C:

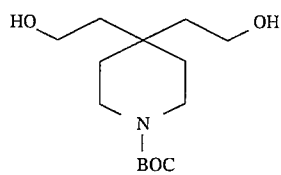

1-t-Butoxycarbonylpiperidine-4,4-diethanol

The benzylamine (2.07 g, 7.9 mmol) was dissolved in methanol (60 mL), BOC$_2$O (1.72 g, 7.9 mmol) added and the mixture hydrogenated at 50 psi over 10% palladium hydroxide on charcoal (200 mg) for 18 hours. The reaction mixture was filtered through celite, washed with methanol and the filtrate evaporated to give 1-t-Butoxycarbonylpiperidine-4, 4-diethanol (2.0 g).

NMR (300 MHz, CDCl$_3$) δ:3.7 (m, 4H), d 3.3 (m, 6H), 1.65 (t, J=6.8 Hz, 4H), 1.41 (s, 9H).

Step D:

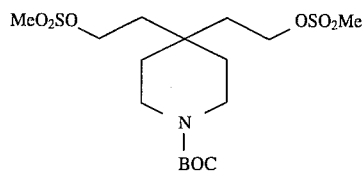

1-t-Butoxycarbonylpiperidine-4,4-diethanol, bis(methanesulfonate)

The diol (2.41 g, 8.9 mmol) was dissolved in dichloromethene (50 mL), the solution cooled to −20° C. under argon before addition of triethylamine (3.7 mL, 26 mmol) and methanesulfonyl chloride (1.6 mL, 20 mmol). After 30 min., the reaction mixture was poured into ice cold 10% citric acid and extracted with ether (X3). The combined extracts were washed with water, saturated NaHCO₃ and brine, dried (MgSO₄) and the solvent evaporated to afford 1-t-Butoxy-carbonylpiperidine-4,4-diethanol, bis(methanesulfonate) (3.2 g).

NMR (300 MHz, CDCl₃) δ: 4.32 (t, J=7.1 Hz, 4H), 3.4 (m, 4H), 3.04 (s, 6H), 1.89 (t, J=7.1 Hz, 4H).

Step E:

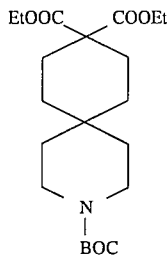

Diethyl 3-t-butyloxycarbonyl-3-azaspiro[5.5]undecane-9,9-dicarboxylate

To a slurry of 60% NaH (2.04 g, 0.51 mole) in toluene (160 mL), under argon, was slowly added diethyl malonate (3.72 mL, 24.3 mmol). The mixture was cooled to 0° C. and the bis-mesylate 1 (7.0 g, 16.3 mmol) added as a solid and the mixture heated to reflux for 18 hours. The reaction was quenched into 10% citric acid (100 mL) and the product extracted with CH₂Cl₂ (2×150 mL). The extracts were dried (Na₂SO₄), concentrated to an oil, and chromatographed on silica to give 3.83 g (60%) of diethyl 3-t-butyloxycarbonyl-3-azaspiro-[5.5]undecane-9,9-dicarboxylate.

¹H NMR (CDCl₃) δ: 1.22 (t, 6H), 1.4 (s, 9H), 2.0 (m, 4H), 3.35 (m, 4H), 4.2 (q, 4H).

Step F:

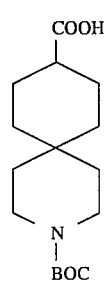

3-t-Butyloxycarbonyl-3-azaspiro[5.5]undecane-9-carboxylic acid

To a solution of the diester 2 (3.69 g, 0.0093 m) in THF (50 mL) was added 1N LiOH (47 mL). The reaction was stirred for 3 days at 25° C., diluted with water (50 mL) and pH adjusted to 2.2 with KHSO₄. The product was extracted into ethyl acetate (2×75 mL), dried (Na₂SO₄), and concentrated to a foam (3.5 g). The solid was melted in a flask at 140° C. for 2 hours, cooled and the oil dissolved in THF (15 mL), 1N LiOH (10 mL) added and mixture stirred overnight at 30° C. The reaction was concentrated to remove THF, diluted with water (20 mL) and washed with diethyl ether (10 mL). The pH was adjusted to 2.5 with KHSO₄ and product extracted (3×50 mL) with ethyl acetate. The extracts were dried (Na₂SO₄), filtered and concentrated to yield 3-t-Butyloxycarbonyl-3-azaspiro[5.5]undecane-9-carboxylic acid as a foam (2.48 g, 90%).

¹H NMR (CDCl₃, partial) δ: 1.45 (s, 9H), 3.4 (m, 4H).

Step G:

(+)-N-[(3R)-2,3-Dihydro-1-methyl-2-oxo-5-phenyl-1H-1,4-benzo-diazepin-3-yl]-1'-(1,1-dimethyl-ethoxycarbonyl)spiro(cyclohexan-4,4'-piperidine)-1-carboxamide m.p. 135°–138° C., [α]_D +58.8° (C=0.925, CHCl₃).

δ_H (CDCl₃) 7.61–7.23 (10H, m), 5.54 (1H, d, J 9.0 Hz), 3.47 (3H, s), 3.37 (4H, m), 2.28 (1H, m), and 1.81–1.18 (21H, s).

Anal. Calcd. for C₃₂H₄₀N₄O₄: C, 70.56; H, 7.40; N, 10.29. Found: C, 70.21; H, 7.40; N, 10.16%.

Employing the procedure substantially as described in Example 43 but substituting an appropriate acid for the 2,3-dihydrobenzofuran-2-carboxylic acid, the following compounds were prepared:

EXAMPLE 41

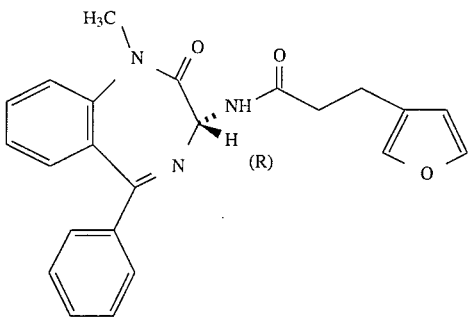

(+)-N-[(3R)-2,3-Dihydro-1-methyl-2-oxo-5-phenyl-
1H-1,4-benzo-diazepin-3-yl]-3-(furan-2-yl)-
propanamide m.p. 115°–118° C., [α]$_D$+65.8° (c=0.800, CHCl$_3$).

δ$_H$ (CDCl$_3$) 7.62–7.26 (11H, m), 6.28 (1H, dd, J 3.2, 2.0 Hz), 6.08 (1H, dd, J 3.2, 0.7 Hz), 5.58 (1H, d, J 8.1 Hz), 3.48 (3H, s), 3.04 (2H, t, J 7.6 Hz), and 2.75 (2H, m).

Anal. Calcd. for C$_{23}$H$_{21}$N$_3$O$_3$.0.3Hexane: C, 72.07; H, 6.15; N, 10.17. Found: C, 71.78; H, 6.30; N, 9.77%.

EXAMPLE 42

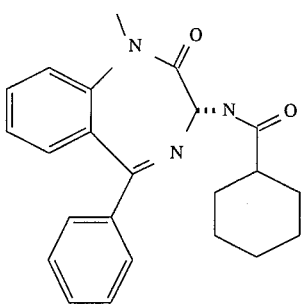

(+)-N-[(3R)-2,3-Dihydro-1-methyl-2-oxo-5-phenyl-
1H-1,4-benzo-diazepin-3-yl]cyclohexylcarboxamide m.p. 213°–214° C., [α]$_D$+62.4° (c=1.000, MeOH).

Anal. Calcd. for C$_{23}$H$_{24}$N$_3$O$_2$: C, 73.77; H, 6.46; N, 11.22. Found: C, 73.86; H, 6.81; N, 11.15%.

EXAMPLE 43

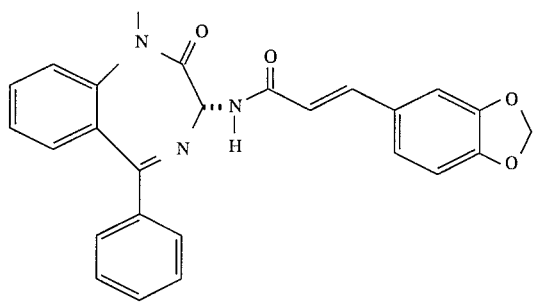

(E)-(+)-N-[(3R)-2,3-Dihydro-1-methyl-2-oxo-5-phenyl-
1H-1,4-benzodiazepin-3-yl]-3-(3,4-methylene-
dioxyphenyl)-2-propenamide m.p. 143°–145° C., [α]$_D$+62.3° (c=0.960, MeOH).

Anal. Calcd. for C$_{25}$H$_{21}$N$_3$O$_4$.0.10H$_2$O.0.20Et$_2$O: C, 69.78; H, 5.27; N, 9.46. Found: C, 69.78; H, 4.98; N, 9.28%.

EXAMPLE 44

(+)-N-[(3R)-2,3-Dihydro-2-methyl-2-oxo-5-phenyl-
1H-1,4-benzo-diazepin-3-yl]-2-(phenylamino)-
acetamide Step A:

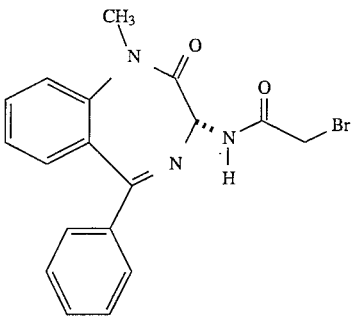

N-[(3R)-2,3-Dihydro-1-methyl-2-oxo-5-phenyl-1H-
1,4-benzodiazepin-3-yl]-2-bromoacetamide Bromoacetyl bromide (165 μL, 383 mg, 1.9 mmol) was added to an ice cooled solution of 3(R)-amino-1,3-dihydro-1-methyl-5-phenyl-2H-1,4-benzodiazepin-2-one (J. Org. Chem. 1987, 52, 3232–3239) (500 mg, 1.88 mmol) and triethylamine (264 μL, 192 mg, 1.9 mmol) in methylene chloride (10 mL) and the mixture was stirred at room temperature for 1 h. The mixture was washed with water (3×10 mL), dried (MgSO$_4$) and the solvent was evaporated under reduced pressure to give N-[(3R)-2,3-dihydro-1-methyl-2-oxo-5-phenyl-1H-1,4-benzodiazepin-3-yl]-2-bromoacetamide as a colorless foam (760 mg, 100%).

δ$_H$ (CDCl$_3$) 8.24 (1H, d, J 7.8 Hz), 7.64–7.24 (9H, m), 5.48 (1H, d, J 7.8 Hz), 4.00 (2H, m), and 3.50 (3H, s).

Step B:

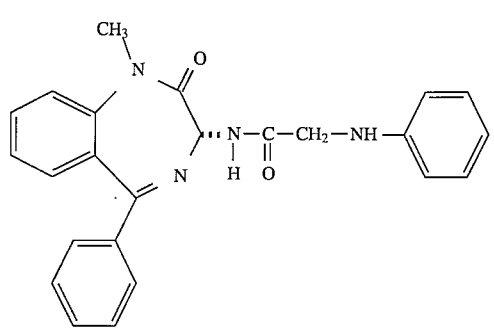

(+)-N-[(3R)-2,3-Dihydro-1-methyl-2-oxo-5-phenyl-1H-1,4-
benzo-diazepin-3-yl]-2-(phenylamino)acetamide Aniline (297 μL, 304 mg, 3.26 mmol) was added to a solution of N-[(3R)-2,3-dihydro-1-methyl-2-oxo-5-phenyl-1H-1,4-benzodiazepin-3yl]-2-bromoacetamide (600 mg, 1.55 mmol) in ethanol (25 mL) and the mixture was heated under reflux for 24 h. The mixture was cooled and the solid was collected and recrystallized from ethanol (20 mL) to give (+)-N-[(3R)-2,3-dihydro-1-methyl-2-oxo-5-phenyl-1H-1,4-benzodiazepin-3-yl]-2-(phenylamino)acetamide as a colorless solid (500 mg, 81%), m.p. 245°–246° C., $[\alpha]_D$+ 119° (C=0.850, CHCl$_3$).

$\delta_H$ (CDCl$_3$) 8.26 (1H, d, J 8.3 Hz), 7.63–7.20 (12H, m), 6.81 (1H, t, J 7.3 Hz), 6.72 (2H, d, J 7.6 Hz), 5.56 (1H, d, J 8.3 Hz), 3.95 (2H, d, J 1.5 Hz), and 3.45 (3H, s).

Anal. Calcd. for C$_{24}$H$_{22}$N$_4$O$_2$: C, 72.34; H, 5.57; N, 14.06. Found: C, 72.37; H, 5.59; N, 14.32%.

Employing the procedure substantially as described above, but substituting 2-chloroaniline or 4-(trifluoromethyl)aniline for the aniline, the following compounds were prepared:

EXAMPLE 45

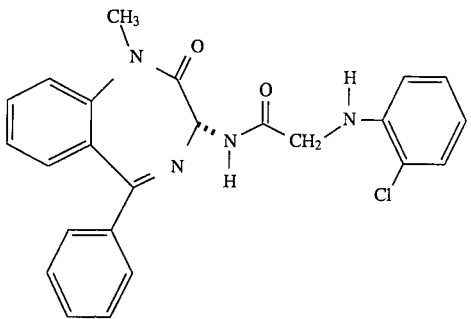

(+)-N-[(3R)-2,3-Dihydro-1-methyl-2-oxo-5-phenyl-1H-1,4-benzo-diazepin-3-yl]-2-(2-chlorophenylamino)acetamide m.p. 222°–224° C., $[\alpha]_D$+111° (c=0.973, CHCl$_3$).

$\delta_H$ (CDCl$_3$) 8.15 (1H, d, J 8.3 Hz), 7.60–7.16 (12H, m), 6.71 (2H, m), 5.57 (1H, d, J 8.3 Hz), 4.01 (2H, d, J 2.7 Hz), and 3.45 (3H, s).

Anal. Calcd. for C$_{24}$H$_{21}$ClN$_4$O$_2$: C, 66.59; H, 4.89; N, 12.94. Found: C, 66.40; H, 4.94; N, 12.92%.

EXAMPLE 46

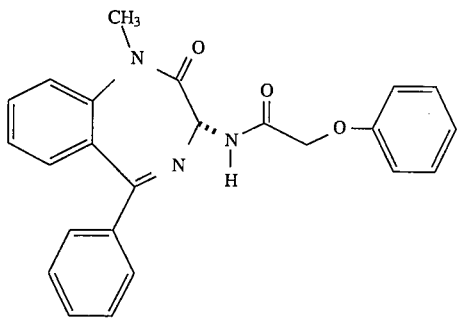

(+)-N-[(3R)-2,3-Dihydro-1-methyl-2-oxo-5-phenyl-1H-1,4-benzo-diazepin-3-yl]-2-(phenoxy)acetamide Phenol (104 mg, 1.1 mmol) was added to a suspension of sodium hydride (60% dispersion in mineral oil, 44 mg, 1.1 mmol) in toluene (10 mL). When hydrogen evolution had stopped, N-[(3R)-2,3-dihydro-1-methyl-2-oxo-5-phenyl-1H-1,4-benzodiazepin-3-yl]-2-bromoacetamide (400 mg, 1.04 mmol) was added and the mixture was stirred at room temperature for 18 h. The mixture was washed with water (3×15 mL), dried (MgSO$_4$) and the solvent was evaporated under reduced pressure. The residue was triturated with 2-propanol and the solid was collected and recrystallized from 2-propanol (5 mL) to give (+)-N-[(3R)-2,3-dihydro-1-methyl-2-oxo-5-phenyl-1H-1,4-benzodiazepin-3-yl]-2-(phenoxy)acetamide as a colorless solid (112 mg, 27%), m.p. 126°–128° C., $[\alpha]_D$+81.6 (C=0.692, CHCl$_3$).

$\delta_H$ (CDCl$_3$) 8.49 (1H, d, J 8.2 Hz), 7.64–7.01 (14H, m), 5.61 (1H, d, J 8.2 Hz), 4.65 (1H, d, J 14.6 Hz), 4.58 (1H, d, J 14.6 Hz), and 3.50 (3H, s).

Anal. Calcd. for C$_{24}$H$_{21}$N$_3$O$_3$: C, 72.17; H, 5.30; N, 10.52. Found: C, 71.84; H, 5.25; N, 10.41%.

Employing the procedure substantially as described above, but substituting 2,4-dichlorophenol, thiophenol or 2,4-dichloro-thiophenol for the phenol, the following compounds were prepared:

EXAMPLE 47

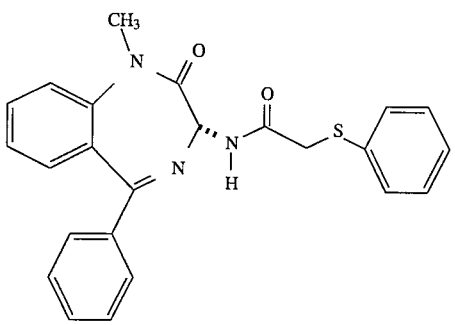

(+)-N-[(3R)-2,3-Dihydro-1-methyl-2-oxo-5-phenyl-1H-1,4-benzo-diazepin-3-yl]-2-(phenylthio)acetamide $[\alpha]_D$+104.9° (c=0.316, CHCl$_3$).

$\delta_H$ (CDCl$_3$) 8.50 (1H, d, J 9.0 Hz), 7.60–7.20 (14H, m), 5.50 (1H, d, J 9.0 Hz), 3.75 (2H, m), and 3.45 (3H, s).

Anal. Calcd. for C$_{24}$H$_{21}$N$_3$O$_2$S: C, 69.37; H, 5.10; N, 10.11. Found: C, 68.98; H, 5.06; N, 9.76%.

EXAMPLE 48

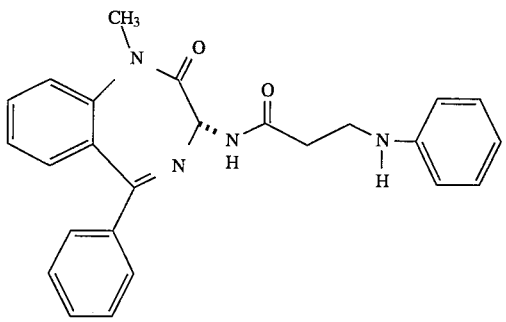

(+)-N-[(3R)-2,3-Dihydro-1-methyl-2-oxo-5-phenyl-1H-1,4-benzo-diazepin-3-yl]-3-(phenylamino)-propanamide 3-Bromopropionyl chloride (2.01 mL, 3.428 g, 20 mmol) was added to an ice cooled solution of 3(R)-amino-1,3-dihydro-1-methyl-5-phenyl-2H-1,4-benzodiazepin-2-one (J. Org. Chem. 1987, 52, 3232–3239) (5.0 g, 18.8 mmol) and triethylamine (2.79 mL, 2.02 mg, 20 mmol) in methylene chloride (85 mL) and the mixture was stirred at room temperature for 18 h. The mixture was washed with saturated aqueous sodium hydrogen carbonate (85 mL), water (2×85 mL), and brine (85 mL), dried (MgSO$_4$) and the solvent was evaporated under reduced pressure. A sample (0.5 g, 1.25 mmol) was dissolved in ethanol (25 mL), aniline (230 μL, 233 mg, 2.5 mmol) was added and the mixture was heated under reflux for 70 h. The mixture was cooled and the solid was collected and recrystallized from ethanol to give (+)-N-[(3R)-2,3-dihydro-1-methyl-2-oxo-5-phenyl-1H-1,4-benzodiazepin-3-yl]-3-(phenylamino)propanamide as a colorless solid, m.p. 218°–221° C., [α]$_D$+58.2° (c=0.585, CHCl$_3$).

δ$_H$ (CDCl$_3$) 7.60–6.71 (16H, m), 5.54 (1H, d, J 8.1 Hz), 3.54 (2H, t, J 6.1 Hz), 3.52 (3H, s), and 2.70 (2H, m).

Anal. Calcd. for C$_{25}$H$_{24}$N$_4$O$_2$.0.5EtOH: C, 71.70; H, 6.25; N, 12.87. Found: C, 71.42; H, 5.98; N, 12.84%.

EXAMPLE 49

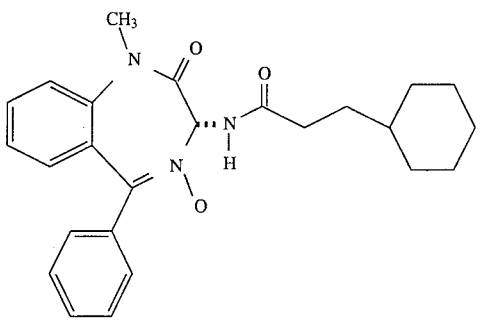

(−)-3-Cyclohexyl-N-[(3R)-2,3-dihydro-1-methyl-2-oxo-4-oxido-5-phenyl-1H-1,4-benzodiazepin-3-yl]propanamide 3-Chloroperoxybenzoic acid (80%, 0.32 g, 1.5 mmol) was added to a solution of (+)-3-cyclohexyl-N-[(3R)-2,3-dihydro-1-methyl-2-oxo-5-phenyl-1H-1,4-benzodiazepin-3-yl]propanamide (0.60 g, 1.5 mmol) in dichloromethane (25 mL) and the mixture was stirred at room temperature for 18 h. Further 3-chloroperoxybenzoic acid (80%, 0.1 g, 0.5 mmol) was added and the mixture was stirred for 24 h. The mixture was washed with saturated aqueous sodium hydrogen carbonate (4×25 mL), water (2×25 mL) and brine (25 mL), dried (MgSO$_4$) and the solvent was evaporated under reduced pressure. The residue was recrystallized from toluene/hexane (65:35) to give (−)-3-cyclohexyl-N-[(3R)-2,3-dihydro-1-methyl-2-oxo-4-oxido-5-phenyl-1H-1,4-benzodiazepin-3-yl]propanamide as colorless prisms, m.p. 222°–224° C., [α]$_D$−80.7° (c=1.15, CHCl$_3$).

δ$_H$ (CDCl$_3$) 7.71–7.23 (10H, m), 6.01 (1H, d, J 9.3 Hz), 3.54 (3H, s), 2.48 (2H, m), and 1.76–0.89 (13H, m).

Anal. Calcd. for C$_{25}$H$_{29}$N$_3$O$_3$.0.5H$_2$O: C, 70.06; H, 7.06; N, 9.81. Found: C, 70.10; H, 6.80; N, 9.79%.

EXAMPLE 50

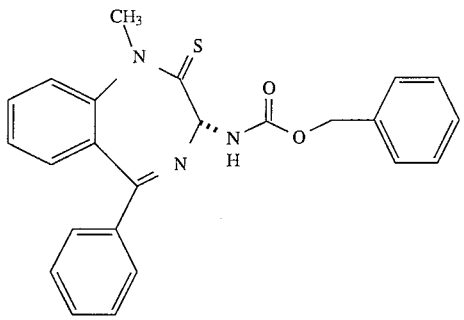

(+)-Phenylmethyl N-[(3R)-2,3-dihydro-1-methyl-5-phenyl-2-thioxo-1H-1,4-benzodiazepin-3-yl]carbamate A mixture of (+)-phenylmethyl N-[(3R)-2,3-dihydro-1-methyl-5-phenyl-2-oxo-1H-1,4-benzodiazepin-3-yl]carbamate (4.0 g, 10 mmol) and 2,4-bis(4-methoxyphenyl)-1,3-dithia-2,4-diphosphetane-2,4disulfide (4.5 g, 11 mmol) in toluene (100 mL) was heated under reflux for 75 min. The mixture was cooled and the volume was reduced to 30 mL by evaporation under reduced pressure. The residue was purified by flash column chromatography on silica gel, eluting with EtOAc/Hexane (75:25) to give (+)-phenylmethyl N-[(3R)-2,3-dihydro-1-methyl-5-phenyl-2-thioxo-1H-1,4-benzodiazepin-3-yl]carbamate as a solid, m.p. 128°–131° C., [α]$_D$+22.5° (c=0.656, CHCl$_3$).

δ$_H$ (CDCl$_3$) 7.65–7.26 (15H, m), 5.50 (1H, d, J 8.8 Hz), 5.14 (2H, s), and 3.86 (3H, s).

Anal. Calcd. for C$_{24}$H$_{21}$N$_3$O$_2$S.0.25H$_2$O: C, 68.63; H, 5.16; N, 10.01. Found: C, 68.28; H, 5.21; N, 10.06%.

EXAMPLE 51

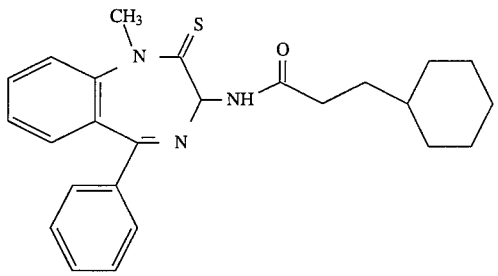

3-Cyclohexyl-N-(2,3-dihydro-1-methyl-5-phenyl-2-thioxo-1H-1,4-benzodiazepin-3-yl)propanamide Hydrogen bromide was bubbled at room temperature through a solution of (+)-phenylmethyl N-[(3R)-2,3-dihydro-1-methyl-5-phenyl-2-thioxo-1H-1,4-benzodiazepin-3-yl]carbamate (0.9 g, 2.1 mmol), acetic acid (5 mL) and dichloromethane (5 mL). After 2 h., the solvent was evaporated under reduced pressure, ether was added and the solid was collected and dried in vacuo. A sample (0.58 g, 1.8 mmol) was suspended in THF (10 mL), triethylamine (0.24 mL, 0.18 g, 1.8 mmol) was added and the mixture was stirred at room temperature for 3 h. In a separate flask, oxalyl chloride (0.20 mL, 0.29 g, 2.3 mmol) was added to a solution of cyclohexanepropionic acid (0.33 mL, 0.30 g, 1.9 mmol) and DMF (1 drop) in THF (10 mL) and the mixture was stirred at room temperature for 3 h. The two mixtures were combined, triethylamine (0.32 mL, 0.23 g, 2.3 mmol) was added and the mixture was stirred at room temperature for 2.5 h. The solvent was evaporated under reduced pressure, water was added and the mixture was extracted with ethyl acetate. The combined organic fractions were washed with water, saturated aqueous sodium hydrogen carbonate, water (2×) and brine, dried (Na$_2$SO$_4$) and the solvent was evaporated under reduced pressure. The residue was purified by flash column chromatography on silica gel, eluting with CH$_2$Cl$_2$/MeOH (99.5:0.5) and the residue was recrystallized from EtOAc/Hexane to give 3-cyclohexyl-N-(2,3-dihydro-1-methyl-5-phenyl-2-thioxo-1H-1,4-benzodiazepin-3-yl-)propanamide as a solid, m.p. 219°–221° C.

$\delta_H$ (CDCl$_3$) 7.95 (1H, br d, J 8.6 Hz), 7.65–7.30 (9H, m), 5.72 (1H, d, J 8.6 Hz), 3.87 (3H, s), 2.41 (2H, t, J 7.6 Hz), and 1.80–0.85 (13H, m).

Anal. Calcd. for C$_{25}$H$_{29}$N$_3$OS.0.25H$_2$O: C, 70.81; H, 7.01;N, 9.91. Found: C, 70.80; H, 6.91; N, 9.95%.

EXAMPLE 52

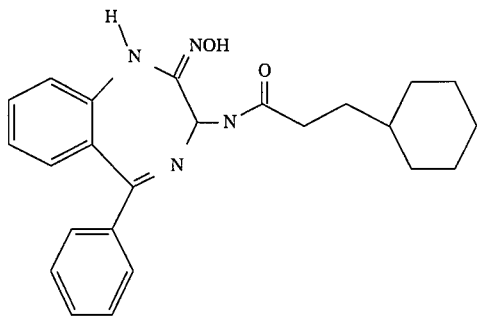

(E)-and (Z)-3-Cyclohexyl-N-(2,3-dihydro-2-hydroxyimino-5-phenyl-1H-1,4-benzodiazepin-3-yl)propanamide A mixture of 3-cyclohexyl-N-(2,3-dihydro-1-methyl-5-phenyl-2-thioxo-1H-1,4-benzodiazepin-3-yl)propanamide (740 mg, 1.83 mmol), hydroxylamine hydrochloride (140 mg, 2 mmol) and triethylamine (280 μL, 203 mg, 2 mmol) in methanol (15 mL)/THF (15 mL) was stirred at room temperature for 3 h. The solvent was evaporated under reduced pressure and the residue was purified by flash column chromatography on silica gel, eluting with CH$_2$Cl$_2$/MeOH (98:2). The residue recrystallized from ethyl acetate. The first isomer to crystallize was recrystallized from ethyl acetate to give (E)-3-cyclohexyl-N-(2,3-dihydro-2-hydroxyimino-5-phenyl-1H-1,4-benzodiazepin-3-yl)propanamide as a solid, m.p. 196° C.

$\delta_H$ (d$_6$-DMSO) 12.20 (1H, s), 9.00 (1H, d, J 8.0 Hz), 7.70–7.30 (10H, m), 5.45 (1H, d, J 8.0 Hz), 2.30 (2H, m), and 1.80–0.75 (13H, m).

The second isomer to crystallize was recrystallized from methanol to give (Z)-3-cyclohexyl-N-(2,3-dihydro-2-hydroxyimino-5-phenyl-1H-1,4-benzodiazepin-3-yl)propanamide as a solid, m.p. 219° C.

$\delta_H$ (d$_6$-DMSO) 9.95 (1H, s), 8.95 (1H, s), 8.75 (1H, d, J 8.0 Hz), 7.50–7.00 (9H, m), 5.70 (1H, d, J 8.0 Hz), 2.25 (2H, m), and 1.75–0.75 (13H, m).

Anal. Calcd. for C$_{24}$H$_{28}$N$_4$O$_2$: C, 71.26; H, 6.98; N, 13.85. FOUND: C, 70.8.9; H, 6.99; N, 13.55%.

EXAMPLE 53

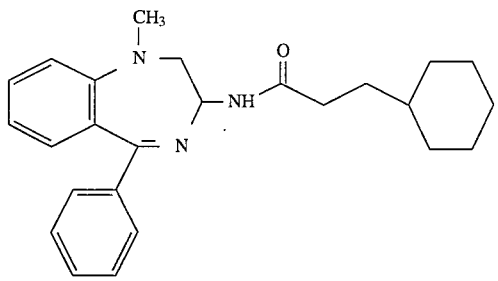

3-Cyclohexyl-N-(2,3-dihydro-1-methyl-5-phenyl-1H-1,4-benzodiazepin-3yl)propanamide Freshly prepared Raney nickel (400 mg) was added to a solution of 3-cyclohexyl-N-(2,3-dihydro-1-methyl-5-phenyl-2-thioxo-1H-1,4-benzodiazepin-3-yl)propanamide (200 mg, 0.5 mmol) in ethanol (20 mL) and the mixture was stirred at room temperature for 2 h. The mixture was filtered and the solvent was evaporated under reduced pressure. The residue was purified by flash column chromatography on silica gel, eluting with CH$_2$C$_2$/MeOH (99.75:0.25) to give 3-cyclohexyl-N-(2,3-dihydro-1-methyl-5-phenyl-1H-1,4-benzodiazepin-3yl) propanamide as a foam.

$\delta_H$ (CDCl$_3$) 7.60–6.80 (9H, m), 6.37 (1H, br d, J 6.6 Hz), 5.53 (1H, m), 3.60 (2H, m), 2.77 (3H, s), 2.21 (2H, t, J 8.0 Hz), and 1.85–0.80 (13H, m).

Anal. Calcd. for C$_{25}$H$_{31}$N$_3$O.0.2CH$_2$Cl$_2$: C, 74.45; H, 7.79; N, 10.34. Found: C, 74.68; H, 7.87; N, 10.23%.

EXAMPLE 54

1-(2,3-Dihydro-1-methyl-2-oxo-5-phenyl-1H-thieno-[2,3-e]-1.4-diazepin-3-yl)-3-(3-methylphenyl)urea Step A:

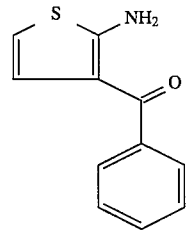

(2-Amino-3-thienyl)phenylmethanone

Triethylamine (6.8 mL, 4.94 g, 49 mmol) was added to a heated (33° C.) mixture of β-oxobenzenepropanenitrile (18.6 g, 128 mmol) and 1,2-dithiane-2,5-diol (9.8 g, 64 mmol) in ethanol (120 mL) and the mixture was stirred at 50° C. for 18 h. The mixture was cooled and the solvent was evaporated under reduced pressure. Dichloromethane was added, the mixture was washed with aqueous hydrochloric acid (0.5M), aqueous sodium hydroxide (1M) and brine, dried (Na$_2$SO$_4$) and the solvent was evaporated under reduced pressure. The residue was recrystallized from acetonitrile (150 mL) to give (2-amino-3-thienyl)-phenylmethanone as an orange solid (5.7 g, 44%).

$\delta_H$ (CDCl$_3$) 7.70–7.35 (5H, m), 6.95 (2H, br s), 6.90 (1H, d, J 6.3 Hz), and 6.15 (1H, d, J 6.3 Hz).

Step B:
2,3-Dihydro-5-phenyl-1H-thieno[2,3-e]-1,4-diazepin-2-one

A solution of 1,3-dihydro-1,3-dioxo-2H-isoindole-2-acetyl chloride (8.6 g, 38 mmol) in dichloromethane (20 mL) was added slowly to a cooled (0° C.) mixture of (2-amino-3-thienyl)phenyl-methanone (6.8 g, 33 mmol), pyridine (6.34 mL, 6.20 g, 78 mmol) and 4-dimethylaminopyridine (0.79 g, 6.5 mmol) in dichloromethane (130 mL). The mixture was stirred at 0° C. for 30 min., diluted with dichloromethane (80 mL) and washed with aqueous hydrochloric acid (1M), saturated aqueous sodium hydrogen carbonate and brine. The mixture was dried (Na$_2$SO$_4$) and the solvent was evaporated under reduced pressure. The residue was triturated with ethanol and the solid was collected and dried in vacuo to give N-(3-benzoylthien-2-yl)-1,3-dihydro-1,3-dioxo-2H-isoindole-2-acetamide as a solid (9.8 g, 76%).

A mixture of N-(3-benzoylthien-2-yl)-1,3-dihydro-1,3-dioxo-2H-isoindole-2-acetamide (10.9 g, 28 mmol) and hydrazine (1.9 mL, 1.94 g, 60 mmol) in THF (500 mL) was heated under reflux for 4 h. The mixture was cooled, filtered and the solvent was evaporated under reduced pressure. Saturated aqueous sodium hydrogen carbonate was added and the mixture was extracted with ethyl acetate. The combined organic fractions were washed with brine, dried (Na$_2$SO$_4$) and the solvent was evaporated under reduced pressure. Acetic acid (300 mL) was added and the mixture was heated under reflux for 15 min. The mixture was cooled and the solvent was evaporated under reduced pressure. Saturated aqueous sodium hydrogen carbonate was added and the mixture was extracted with ethyl acetate. The combined organic fractions were washed with brine, dried (Na$_2$SO$_4$) and the solvent was evaporated under reduced pressure to give 2,3-dihydro-5-phenyl-1H-thieno[2,3-e]-1,4-diazepin-2-one as a foam (3.5 g, 52%).

$\delta_H$ (CDCl$_3$) 9.75 (1H, br s), 7.90–7.30 (5H, m), 6.87 (1H, d, J 6.0 Hz), 6.82 (1H, d, J 6.0 Hz), and 4.45 (2H, s).

Step C:

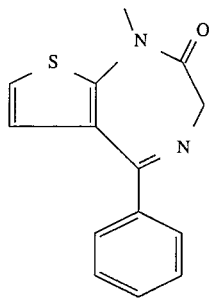

2,3-Dihydro-1-methyl-5-phenyl-1H-thieno[2,3-e]-1,4-diazepin-2-one

Sodium hydride (60% dispersion in mineral oil, 757 mg, 11.3 mmol) was added to a cooled (0° C.) solution of 2,3-dihydro-5-phenyl-1H-thieno[2,3-e]-1,4-diazepin-2-one (2.61 g, 10.8 mmol) in DMF (7 mL). Further DMF (10 mL) was added and the mixture was stirred for 30 min. A solution of iodomethane (0.67 mL, 1.53 g, 10.8 mmol) in ether (20 mL) was added and the mixture was stirred for 1 h. The mixture was poured into water and the mixture was extracted with ethyl acetate. The combined organic fractions were washed with brine, dried (Na$_2$SO$_4$) and evaporated under reduced pressure. The residue was purified by flash column chromatography on silica gel, eluting with CH$_2$Cl$_2$/MeOH (95:5) to give 2,3-dihydro-1-methyl-5-phenyl-1H-thieno[2,3-e]-1,4-diazepin-2-one (1.5 g, 54%). $\delta_H$ (CDCl$_3$) 7.67–7.35 (5H, m), 7.00 (1H, d, J 6.0 Hz), 6.85 (1H, d, J 6.0 Hz), 4.45 (2H, br s), and 3.50 (3H, s).

Step D:

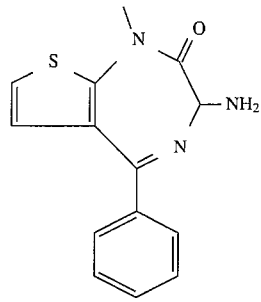

3-Amino-2,3-dihydro-1-methyl-5-phenyl-1H-thieno[2,3-e]-1,4-diazepin-2-one 2,3-Dihydro-1-methyl-5-phenyl-1H-thieno[2,3-e]-1,4-diazepin-2-one (1.5 g, 5.8 mmol) was dissolved in toluene (30 mL). The mixture was cooled to −10° C. and potassium t-butoxide (1.7 g, 15.1 mmol) was added. The mixture was stirred at 31 10° C. for 15 min., then isoamyl nitrite (1.0 mL, 0.87 g, 7.4 mmol) was added. The mixture was stirred at −10° C. for 1 h. then allowed to warm to room temperature and poured into water (50 mL) and acetic acid (3 mL). The mixture was extracted with ethyl acetate and the combined organic fractions were washed with brine, dried (Na$_2$SO$_4$) and the solvent was evaporated under reduced pressure. The residue was purified by flash column chromatography on silica gel, eluting with EtOAc/Hexane to give 2,3-dihydro-1-methyl-3-hydroxyimino-5-phenyl-1H-thieno[2,3-e]-1,4-diazepin-2-one (0.80 g, 48%).

2,3-Dihydro-1-methyl-3-hydroxyimino-5-phenyl-1H-thieno[2,3-e]-1,4-diazepin-2-one (0.80 g, 2.8 mmol) was dissolved in ethanol (40 mL) and Raney nickel (2 g) was added. The mixture was shaken under hydrogen (50 p.s.i.) for 5 days, adding further Raney nickel (10 g) in portions. The mixture was filtered and the solvent was evaporated under reduced pressure. The residue was purified by flash column chromatography on silica gel, eluting with CH$_2$Cl$_2$/MeOH to give 3-amino-2,3-dihydro-1-methyl-5-phenyl-1H-thieno[2,3-e]-1,4-diazepin-2-one (248 mg, 33%).

$\delta_H$ (CDCl$_3$) 7.50–7.30 (5H, m), 7.05 (1H, d, J 6.0 Hz), 6.85 (1H, d, J 6.0 Hz), 4.57 (1H, s), 3.55 (3H, s), and 1.70 (2H, br s).

Step E:

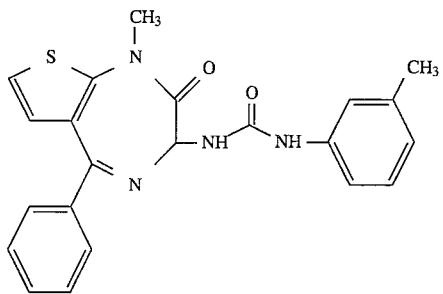

1-(2,3-Dihydro-1-methyl-2-oxo-5-phenyl-1H-thieno[2,3-e]-1,4-diazepin-3-yl)-3-(3-methylphenyl)urea 3-Methylphenylisocyanate (60 µL, 62 mg, 0.46 mmol) was added to a solution of 3-amino-2,3-dihydro-1-methyl-5-phenyl-1H-thieno[2,3-e]-1,4-diazepin-2-one (124 mg, 0.46 mmol) in tetrahydro-furan (5 mL). The mixture was stirred at room temperature for 2 h. and the solvent was evaporated under reduced pressure. The residue was crystallized from EtOAc (4 mL) to give 1-(2,3-dihydro-1-methyl-2-oxo-5-phenyl-1H-thieno[2,3-e]-1,4-diazepin-3-yl)-3-(3-methyl-phenyl)urea as a solid (94 mg, 50%).

m.p. 128°–130° C.

$\delta_H$ (CDCl$_3$) 8.70 (1H, s), 7.65–6.75 (12H, m), 5.55 (1H, d, J 9.0 Hz), 3.55 (3H, s), and 2.30 (3H, s).

Anal. Calcd. for C$_{22}$H$_{20}$N$_4$O$_2$S.0.25H$_2$O: C, 64.62; H, 4.99; N, 13.70. Found: C, 64.68; H, 4.96; N, 13.70%.

EXAMPLE 55

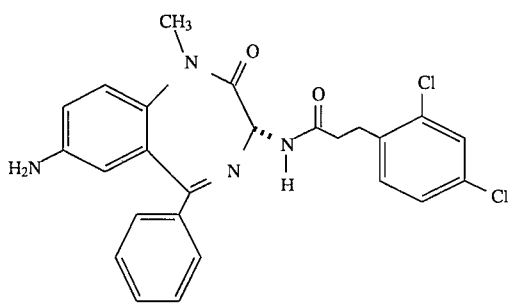

(+)-N-[(3R)-7-Amino-2,3-dihydro-1-methyl-2-oxo-5-phenyl-1H-1,4-benzodiazepin-3-yl]-3-(2,4-dichlorophenyl)propanamide Step A:

To a mixture of 3(R)-amino-1,3-dihydro-1-methyl-5-phenyl-2H-1,4-benzodiazepin-2-one (J. Org. Chem. 1987, 52, 3232–3239) (3.98 g, 15.0 mmol) in concentrated sulfuric acid (15 mL) cooled in an ice-bath was added dropwise a solution of potassium nitrate (2.12 g, 21.0 mmol) in concentrated sulfuric acid (6 mL). The mixture was stirred with cooling for 2 h., then stirred at ambient temperature for 1.5 h. Ice (80 g) was added and the mixture was basified with concentrated ammonium hydroxide to pH 9. The resulting mixture was extracted with ethyl acetate (3×220 mL). The combined organic fractions were washed with brine, dried (Na$_2$SO$_4$) and the solvent was evaporated under reduced pressure. The residue was purified by flash column chromatography on silica gel, eluting with chloroform/methanol (97:3). The material which eluted was further purified by flash column chromatography on silica gel, eluting with ethyl acetate/methanol (95:5). The material which eluted was stirred under n-butyl chloride (30 mL) and the solvent was evaporated under reduced pressure to give an inseparable mixture of 3(R)-amino-1,3-dihydro-1-methyl-7-nitro-5-phenyl-2H-1,4-benzodiazepin-2-one and 3(R)-amino-1,3-dihydro-1-methyl-7-nitro-5-(2-nitrophenyl)-2H-1,4-benzodiazepin-2-one (3.81 g) in a 3:1 ratio as a yellow solid.

$\delta_H$ (CDCl$_3$) (mononitro compound) 8.43 (1H, dd, J 9, 3 Hz), 8.23 (1H, d, J 3 Hz), 7.59 (2H, m), 7.52 (2H,m), 7.44 (2H,m), 4.47 (1H,s), 3.53 (3H,s), and 2.42 (2H, br s); (dinitro compound) 8.49 (1H, dd, J 9, 3), 8.42 (1H, m), 8.18 (1H, d, J 3 Hz), 8.01 (1H, m), 7.67 (1H, t, J 6 Hz), 7.6–7.4 (2H, m), 4.52 (1H,s), 3.56 (3H,s), and 2.42 (2H, br s).

Step B:

A solution of 3-(2,4-dichlorophenyl)propionic acid (482 mg, 2.2 mmol), DMF (0.017 mL, 0.22 mmol), and thionyl chloride (0.24 mL, 3.3 mmol) in chloroform (2.5 mL) was heated at reflux for 1 h. The solvent was evaporated under reduced pressure to give 3-(2,4-dichlorophenyl)propionyl chloride (520 mg, 100%). To a solution of mixed 3(R)-amino-1,3-dihydro-1-methyl-7-nitro-5-phenyl-2H-1,4-benzodiazepin-2-one and 3(R)-amino-1,3-dihydro-1-methyl-7-nitro-5-(2-nitrophenyl)-2H-1,4-benzodiazepin-2-one (3:1) (621 mg, 2 mmol) and triethylamine (0.305 mL, 2.2 mmol) in methylene chloride (10 mL), was added a solution of 3-(2,4-dichlorophenyl)propionyl chloride (520 mg, 2.2 mmol) in methylene chloride (1.5 mL). The mixture was stirred for 30 min., the solvent was partially evaporated under reduced pressure, and the reaction mixture was purified by flash column chromatography on silica gel, eluting with methylene chloride/ether (90:10) to give a mixture of (+)-N-[(3R)-2,3-dihydro-1-methyl-7-nitro-2-oxo-5-phenyl-1H-1,4-benzodiazepin-3-yl]-3-(2,4-dichlorophenyl)-propanamide and (+)-N-[(3R)-2,3-dihydro-1-methyl-7-nitro-2-oxo-5-(2-nitrophenyl)-1H-1,4-benzodiazepin-3-yl]-3-(2,4-dichlorophenyl)-propanamide (850 mg, 84%) in a 3:1 ratio as a solid white foam.

$\delta_H$ (CDCl$_3$) (mononitro compound) 8.45 (1H, dd, J 9, 3 Hz), 8.25 (1H, d J 3 Hz), 7.54 (3H, m), 7.45 (2H, m), 7.38 (1H, d, J 2 Hz), 7.26–7.18 (4H, m), 5.50 (1H, d, J 8 Hz), 3.52 (3H, s), 3.10 (2H, m), and 2.70 (2H, m); (dinitro compound) 8.51 (1H, dd, J 9, 3 Hz), 8.40 (1H, m), 8.21 (1H, d J 3 Hz), 7.98 (1H, m), 7.68 (1H, t, J 6 Hz), 7.60 (1H, m), 7.44 (1H, m), 7.26–7.15 (4H, m), 5.52 (1H, d, J 8 Hz), 3.55 (3H, s), 3.10 (2H, m), and 2.70 (2H, m).

Step C:

To a solution of mixed N-[(3R)-2,3-dihydro-1-methyl-7-nitro-2-oxo-5-phenyl-1H-1,4-benzodiazepin-3-yl ]-3-(2,4-dichlorophenyl)propanamide and (+)-N-[(3R)-2,3-dihydro-1-methyl-7-nitro-2-oxo-5-(2-nitrophenyl)-1H-1,4-benzodiazepin-3-yl]-3-(2,4-dichlorophenyl)propanamide (3:1) (770 mg, 1.5 mmol) in acetic acid (6 mL) was added dropwise in portions over 1.5 h. a solution of 15% titanium (III) chloride in 20–30% hydrochloric acid (7.8 mL, 9.0 mmol). The resulting solution was stirred 30 min., basified with 20% sodium hydroxide solution (pH 9), diluted with water (80 mL) and extracted with ethyl acetate (3×100 mL). The combined organic fractions were washed with brine, dried (Na$_2$SO$_4$) and the solvent was evaporated under reduced pressure. The residue was purified by flash column chromatography on silica gel, eluting with ethyl acetate/hexane (75:25 increasing to 100:0). The first compound to elute was crystallized from ethyl acetate to give (+)-N-[(3R)-7-amino-2,3-dihydro-1-methyl-2-oxo-5-phenyl-1H-1,4-benzodiazepin-3-yl]-3-(2,4-dichlorophenyl)-propanamide (413 mg, 57%) as a pale yellow solid, m.p. 179°–180° C., [$\alpha$]$_D$+60.2° (c=0.500, CHCl$_3$).

$\delta_H$ (CDCl$_3$) 7.60 (2H, d, J 7 Hz), 7.49–7.36 (5H, m) 7.24 (1H, d, J 9 Hz), 7.17 (2H, m), 6.99 (1H, dd, J 9, 3 Hz), 6.64 (1H,d, J 3 Hz), 5.54 (1H, d, J 8 Hz), 4.80–3.50 (2H, br s), 3.39 (3H, s), 3.09 (2H, t, J 8 Hz), and 2.68 (2H, dt, J$_d$ 3, J$_t$ 8 Hz).

Anal. Calcd. for C$_{25}$H$_{22}$Cl$_2$N$_4$O$_2$: C, 62.38; H, 4.61; N, 11.64. Found: C, 62.58; H, 4.68; N, 11.65%.

The second compound to elute was crystallized from ethyl acetate to give (+)-N-[(3R)-7-amino-2,3-dihydro-1-methyl-2-oxo-5-(2-aminophenyl)-1H-1,4-benzodiazepin-3-yl]-3-(2,4-dichlorophenyl)propanamide (114 mg, 15%) as a pale yellow solid, m.p. 188°–189° C., [$\alpha$]$_D$50.0° (c=0.100, MeOH).

$\delta_H$ (CDCl$_3$) 7.36 (2H, m), 7.25 (1H, d, J 9 Hz), 7.15 (3H, m), 7.00 (1H, m), 6.88 (2H, m), 6.79 (1H, m), 6.60 (1H, bs), 5.52 (1H, d, J 8 Hz), 4.10–2.80 (4H br s), 3.40 (3H, m), 3.09 (2H, t, J 8 Hz), and 2.69 (2H, m).

Anal. Calcd. for C$_{25}$H$_{23}$Cl$_2$N$_5$O$_2$.0.05EtOAc: C, 60.43; H, 4.71; N, 13.99. Found: C, 60.79; H, 4.74; N, 13.83%.

EXAMPLE 56

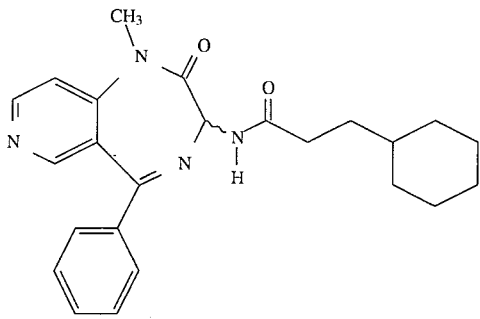

N-(2,3-Dihydro-1-methyl-2-oxo-5-phenyl-1H-pyrido-[4,3-e]-1,4-diazepin-3-yl)-3-(cyclohexyl)propanamide A solution of dicyclohexylcarbodiimide (87 mg, 0.42 mmol) in methylene chloride (0.17 mL) was added to a solution of 3-amino-2,3-dihydro-1-methyl-5-phenyl-1H-pyrido[4,3-e]-1,4-diazepine-2-one (93 mg, 0.35 mmol) and cyclohexanepropionic acid (0.065 mL, 0.38 mmol) in tetrahydrofuran (0.5 mL) under argon. The resulting mixture was stirred for 5 h., filtered, and the filtrate was evaporated under reduced pressure. The residue was purified by preparative plate chromatography on silica gel eluting with methanol/chloroform/acetic acid (5:95:1). The purified material was stirred under chloroform (5 mL) with potassium carbonate (0.1 g) and water (2 drops) for 5 min. The mixture was dried (Na$_2$SO$_4$) and the solvent was evaporated under reduced pressure. The residue was crystallized from toluene to give N-(2,3-dihydro-1-methyl-2-oxo-5-phenyl-1H-pyrido[4,3-e]-1,4-diazepin-3-yl)-3-(cyclohexyl)-propanamide (47 mg, 33%) as a white crystalline solid, m.p. 170°–173° C.

$\delta_H$ (CDCl$_3$) 8.75 (1H, d, J 6 Hz), 8.61 (1H, s), 7.58 (2H, m), 7.52 (1H, m), 7.45 (2H, m), 7.31 (1H, d, J 6 Hz), 7.21 (1H, d, J 8 Hz), 5.54 (1H, d, J 8 Hz), 3.51 (3H, s), 2.39 (2H, m), 1.73 (4H, m), 1.63 (3H, m), 1.85–1.12 (4H, m), and 0.94 (2H, m).

Anal. Calcd. for C$_{24}$H$_{28}$N$_4$O$_2$.0.10PhCH$_3$: C, 71.70; H, 7.02; N, 13.54. Found: C, 71.78; H, 7.01; N, 13.57%.

Employing the procedure substantially as described above, but substituting 3-(4-trifluoromethylphenyl)-propionic acid for the cyclohexanepropionic acid, the following compound was prepared:

EXAMPLE 57

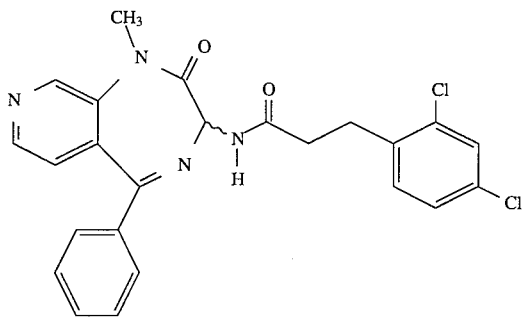

N-(2,3-Dihydro-1-methyl-2-oxo-5-phenyl-1H-pyrido-[3,4-e]-1,4-diazepin-3-yl)-3-(2,4-dichlorophenyl)-propanamide Step A:

To a solution of 2,3-dihydro-1-methyl-5-phenyl-1H-pyrido[3,4-e]-1,4-diazepine-2-one (Can. J. Chem. 1987, 65, 1158–1161) (1.43 g, 5.7 mmol) in toluene (28 mL) under argon cooled to –20° C. (ice/methanol bath) was added potassium t-butoxide (1.59 g, 14.2 mmol). The resulting purple suspension was stirred 15 min. at –20° C. and isoamyl nitrite (0.92 mL, 6.8 mmol) was added. The mixture was stirred at –20° C. for 30 min., then poured into a mixture of water (25 mL), acetic acid (2.5 mL), and ethyl acetate (55 mL). The mixture was stirred to dissolve all solids and the layers were separated. The aqueous layer was extracted with ethyl acetate (2×55 mL). The combined organic fractions were washed with saturated sodium bicarbonate solution and brine (20 mL each), dried (Na$_2$SO$_4$), and the solvent was evaporated under reduced pressure. The residue was triturated with hexane and the solid was collected and dried in vacuo to give 2,3-dihydro-3-hydroxyimino-1-methyl-5-phenyl-1H-pyrido[3,4-e]-1,4-diazepine-2-one (1.60 g, 100%) as a tan foam.

$\delta_H$ (CDCl$_3$) 8.77 (1H, s), 8.50 (1H, d, J 4 Hz), 7.81 (2H, dd, J 8, 1 Hz), 7.60 (1H, m), 7.49 (3H, m), 7.32 (1H, d, J 5 Hz), and 3.55 (3H,s).

Step B:

A solution of stannous chloride dihydrate (3.72 g, 16.5 mmol) in concentrated hydrochloric acid (11 mL) was added dropwise to 2,3-dihydro-3-hydroxyimino-1-methyl-5-phenyl-1H-pyrido[3,4-e]-1,4-diazepine-2-one (1.54 g, 5.5 mmol) cooled in an ice bath. The resulting solution was stirred at ambient temperature for 3 h. The solution was diluted with water (20 mL), basified with concentrated ammonium hydroxide (18 mL), and extracted with ether (4×75 mL). The combined organic fractions were washed with brine (30 mL), dried (Na$_2$SO$_4$), and the solvent was evaporated under reduced pressure. The residue was purified by flash column chromatography on silica gel, eluting with methanol/chloroform/acetic acid (5:95:1 increasing to 10:90:1). The material which eluted was stirred under chloroform (20 mL) with potassium carbonate (0.3 g) and water (2 drops) for 5 min. The mixture was dried (Na$_2$SO$_4$) and the solvent was evaporated under reduced pressure. The residue was stirred under hexane, and the resulting solid was collected to give 3-amino-2,3-dihydro-1-methyl-5-phenyl-1H-pyrido[3,4-e]-1,4-diazepine-2-one (241 mg, 16%) as a yellow solid, m.p. 94°–118° C.

$\delta_H$ (CDCl$_3$) 8.79 (1H, s), 8.48 (1H, d, J 5 Hz), 7.62 (2H, dd, J 8, 1 Hz), 7.51 (1H, m), 7.45 (2H, m), 7.24 (1H, dd, J 5, 1 Hz), 4.47 (1H , s), 3.55 (3H, s), and 2.2 (2H, bs).

Anal. Calcd. for C$_{15}$H$_{14}$N$_4$O.0.25(C$_2$H$_5$)$_2$: C, 67.46; H, 5.84; N, 19.67. Found: C, 67.28; H, 5.66; N, 19.53%. High res. mass spectrum: Theoretical mass for C$_{15}$H$_{14}$N$_4$O (M+1): 267.124586. Measured mass (M+1): 267.123093.

Step C:

A solution of oxalyl chloride (0.023 mL, 0.26 mmol) in methylene chloride (0.2 mL) was added dropwise to a solution of 3-(2,4-dichlorophenyl)propionic acid (48 mg, 0.22 mmol) and DMF (1 drop) in methylene chloride (0.5 mL) cooled in an ice-bath. The resulting solution was stirred 1 h. with cooling. The solvent was evaporated under reduced pressure to give 3-(2,4-dichlorophenyl)-propionyl chloride (52 mg, 100% ). To a solution of 3-amino-2,3-dihydro-1-methyl-5-phenyl-1H-pyrido[3,4-e]-1,4-diazepine-2-one (53 mg, 0.20 mmol) and pyridine (0.021 mL, 0.22 mmol) in methylene chloride (3 mL), was added a solution of 3-(2, 4-dichlorophenyl)-propionyl chloride (52 mg, 0.22 mmol) in methylene chloride (0.5 mL). The mixture was stirred for 1 h., the solvent was partially evaporated under reduced pressure, and the reaction mixture was purified by flash column chromatography on silica gel, eluting with methanol/ether (5:95 increasing to 7.5:92.5). The material which eluted was crystallized from toluene/hexane to give N-(2,3-dihydro-1-methyl-2-oxo-5-phenyl-1H-pyrido[3,4-e]-1,4-diazepin-3-yl)-3-(2,4-dichlorophenyl)propanamide (38 mg, 38%) as a white crystalline solid, m.p. 220°–221° C.

$\delta_H$ (CDCl$_3$) 8.81 (1H, s), 8.52 (1H, d, J 5 Hz), 7.56 (2H, dd, J 7, 2 Hz), 7.51 (1H, m), 7.44 (2H, d, J 6 Hz), 7.40 (1H, m), 7.27 (2H, m), 7.18 (2H, dd, J 8, 2 Hz), 5.48 (1H ,d, J 8 Hz), 3.55 (3H, s), 3.10 (2H, t, J 7 Hz), and 2.71 (2H, dt, J$_d$ 2 J$_t$ 8 Hz).

Anal. Calcd. for $C_{24}H_{20}Cl_2N_4O_2 \cdot 0.25PhCH_3$: C, 63.06; H, 4.52; N, 11.43. Found: C, 63.03; H, 4.48; N, 11.25%.

EXAMPLE 58

N-[2,3-Dihydro-1-methyl-2-oxo-5-isopropyl-1H-1,4-benzodiazepin-3-yl]-3-(2,4-dichlorophenyl)propanamide Step A:

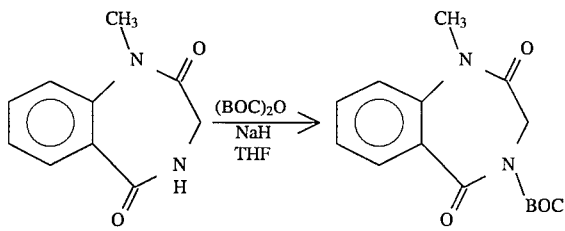

To a solution of the benzodiazipene (1.0 g, 5.3 mmol) in THF (20 mL) at −78° C. under argon was added 60% NaH (0,252 g, 6.3 mmol) and the mixture stirred at −78° C. for ½ hour. The reaction was then allowed to warm to 25° C. and stirred for 2 hours before quenching into cold aq. NH$_4$Cl (10%) and extracting the product into ethyl acetate (3×50 mL). Concentration of the dried (Na$_2$SO$_4$) extracts gave an oil which was passed through silica (EtOAc/hexane) to give 1.35 g product (89%). $^1$H NMR (CDCl$_3$) δ:1.60 (s, 9H), 3.40 (s, 3H), 3.95 (brd, 1H), 4.80 (brd, 1H), 7.20 (d, 1H), 7.30 (q, 1H), 7.60 (t, 1H), 7.92 (d, 1H).

Step B:

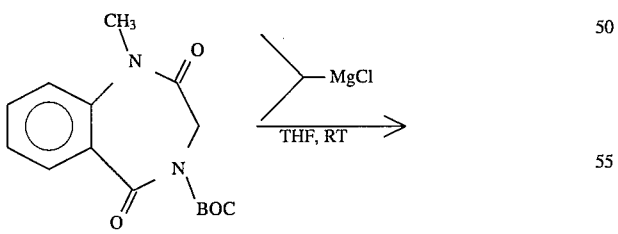

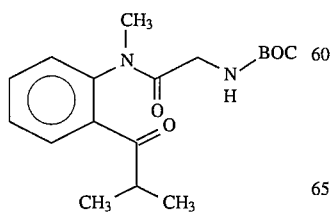

To a solution of the BOC-benzodiazapine (4.0 g, 13.8 mmol) in THF (80 mL) under argon was rapidly added a solution of isopropylmagnesium chloride (2.0M) in THF (7.66 mL, 15.3 mmol). The reaction was stirred to ½ hour, quenched into aq NH$_4$Cl (50 mL), and extracted with ethyl acetate (2×200 mL). The organic extracts were concentrated and chromatographed on silica (1:1, EtOAC/hexane) to give 1.55 g (34%) of product.

$^1$H NMR (CDCl$_3$) δ:1.14 (d, 3H), 1.19 (d, 3H), 1.40 (s, 9H), 3.13 (s, 3H), 3.2–3.8 (m, 3H), 5.45 (brs, 1H), 7.28 (dt, 1H), 7.48 (dt, 1H), 7.56 (dt, 1H), 7.72 (dd, 1H).

Step C:

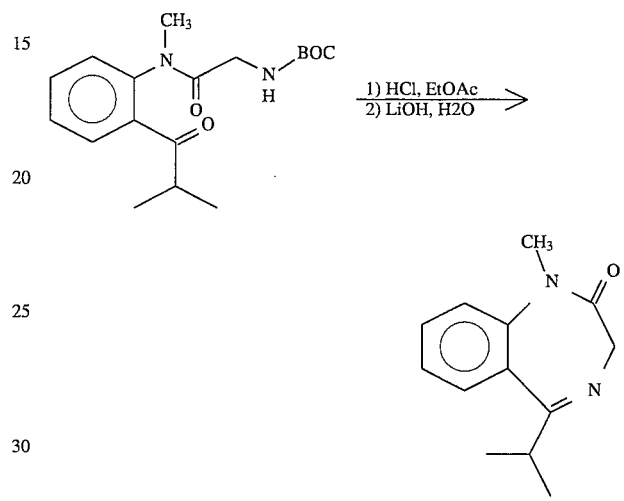

To a 0° C. solution of the isopropylphenone (1.55 g) in ethyl acetate was added anhydrous HCl gas over 90 min. The reaction was then concentrated in vacuo so a solid which was dissolved in H$_2$O (40 mL) and the pH adjusted to 11.0 with 1N LiOH. After 30 min. at pH=11.0 the pH was adjusted to 7.0 with 1N HCl and product extracted into ethyl acetate. The organic extracts were dried (Na$_2$SO$_4$), filtered and concentrated to give a solid 1.22 g, 100%.

$^1$H NMR (CDCl$_3$) δ: 0.95 (d, 3H), 1.30 (d, 3H), 3.16 (septet, 1H), 3.36 (s, 3H), 3.60 (d, 1H), 4.60 (d, 1H), 7.2–7.3 (m, 2H), 7.45–7.55 (m, 2H).

Steps D–F:

The benzodiazepine was (D) converted to the corresponding oxime, (E) reduced and (F) coupled with (2,4-dichlorophenyl)-propionic acid as described in Example 80, Steps A, B and C respectively to yield N-[2,3-dihydro-1-methyl-2-oxo-5-isopropyl-1H-1,4-benzodiazepin-3-yl[-3-(2,4-dichlorophenyl)-propanamide.

m.p. 173°–174° C.

$^1$H NMR (CDCl$_3$) δ: 0.92 (d, 3H), 1.25 (d, 3H), 2.65 (dt, 2H), 3.05 (t, 2H), 3.15 (SepT, 1H), 3.40 (s, 3H), 5.38 (d, 1H), 7.0–7.6 (m, 8H).

The following compounds were prepared in a similar manner as described in Example 81.

EXAMPLE 59

N-[2,3-dihydro-1-methyl-2-oxo-5-isopropyl-1H-1,4-benzodiazepin-3-yl]-3-cyclohexylopropanamide m.p. 164°–165° C. CHN: Anal. Calcd. for C, 71.51; H, 8.46; N, 11.37 Observed: C, 71.72; H, 8.39; N, 11.32

EXAMPLE 60

N-[2,3-dihydro-1-methyl-2-oxo-5-isopropyl-1H-1,4-benzodiazepin-3-yl]-3-(4-trifluoromethylphenyl)-propanamide m.p. 187°–188° C.

$^1$H NMR (CDCl$_3$) δ: 0.92 (d, 3H), 1.25 (d, 3H), 2.66 (dt, 2H), 3.04 (t, 2H), 3.15 (SepT, 1H), 3.40 (S, 3H), 5.38 (d, 1H), 7.14 (brd, 1H), 7.25–7.6 (m, 8H)

EXAMPLE 61

N-[2,3-dihydro-1-methyl-2-oxo-5-(2-furanyl)-1H-1,4-benzodiazepin-3-yl]-3-cyclohexylpropanamide m.p. 168°–169° C. CHN: Anal. Calcd. for C, 70.21; H, 6.92; N, 10.68 Observed: C, 70.15; H, 6.67; N, 10.64

EXAMPLE 62

N-[2,3-dihydro-1-methyl-2-oxo-5-(2-furanyl)-1H-1,4-benxodiazepin-3-yl]-3-(4-trifluoromethylphenyl)-propanamide m.p. 155°–157° C. CHN: Anal. Calcd. for C, 63.29; H, 4.432; N, 9.23 Observed: C, 63.22; H, 4.44; N, 9.07

EXAMPLE 63

N-[2,3-dihydro-1-methyl-2-oxo-5-(2-furanyl)-1H-1,4b-enzodiazepin-3-yl]-3-(2,4-dichlorophenyl)propanamide m.p. 132°–133° C.

CHN: Anal. Calcd. for C, 60.54; H, 4.20; N, 9.21 Found: C, 60.62; H, 4.07; N, 9.07

EXAMPLE 64

N-[2,3,4,5-tetrahydro-1-methyl-2-oxo-5-isopropyl-1H-1,4-benzo-diazepin-3yl]-3-cyclohexylpropanamide

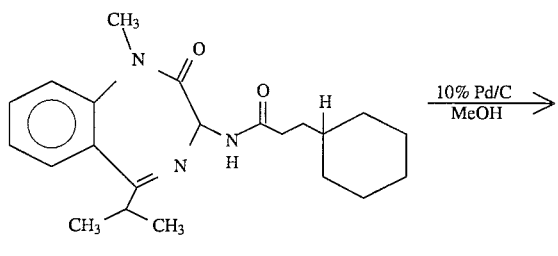

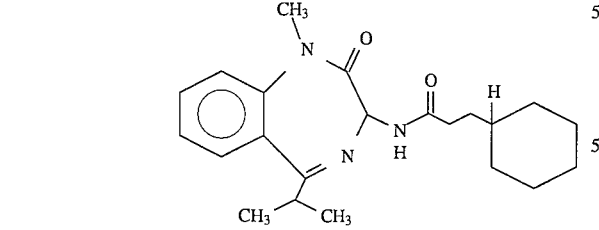

A solution of N-[2,3-dihydro-1-methyl-2-oxo-5-isopropyl-1H-1,4-benzodiazepin-3-yl]-3-cyclohexylpropanamide (50 mg) in methanol (10 mL), containing 10% Pd/C (50 mg) was stirred under 1 atmosphere of hydrogen for 18 hours. Filtration of the reaction, concentration and crystallization from diethyl ether gave 21 mg N-[2,3,4,5-tetrahydro-1-methyl-2-oxo-5-isopropyl-1H-1,4-benzodiazepin-3-yl]-3-cyclohexylpropanamide.

CHN: Anal. Calcd. for C,71.12; H, 8.95; N, 11.31 Observed: C,70.98; H, 8.97; N, 11.15 m.p. 114°–115° C.

EXAMPLE 65

N-[2,3-dihydro-1-methyl-2-oxo-5-methyl-1H-1,4-benzodiazepin-3-yl]-3-(2,4-dichlorophenyl)-propanamide Step A:

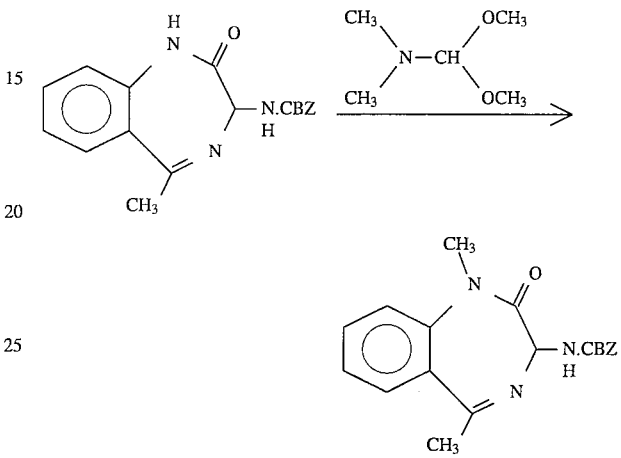

To CBZ-benzodiazapene (250 mg, 0.776 mmol) in toluene (25 mL) at reflux was added dropwise a solution of DMF dimethylacetal (1.09 mL) in toluene (10 mL). The reaction was refluxed for 5 hours, cooled and concentrated to an oil. The oil was triturated with ether to give a white solid (124 mg).

$^1$H NMR (CDCl$_3$) δ: 2.50 (s, 3H), 3.42 (S, 3H), 5.12–5.20 (m,. 3H)<6.62 (d, 1H), 7.25–6.4 (m, 7H), 7.5–7.6 (m, 2H).

Step B:

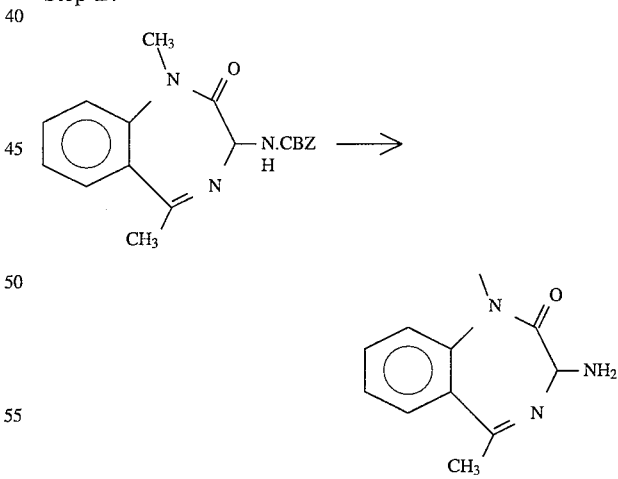

The CBZ-amine-N-methyl amide (190 mg) was treated with 30% HBr/AcOH (0.8 mL) for 1 hour at room temperature. The reaction mixture was poured into ether (10 mL) at 0° C. and the solid filtered. Solid dissolved in 10% Aq. NaOH (5 mL/and CH$_2$Cl$_2$ (10 mL) and organic layer separated, dried (Na$_2$SO$_4$), filtered and concentrated to an oil (172 mg, 110%).

$^1$H NMR (CDCl$_3$) δ: 2.42 (s, 3H), 3.05 (brs, 2H), 3.40 (s, 3H), 4.40 (s, 1H), 7.2–7.6 (m, 4H).

Step C:

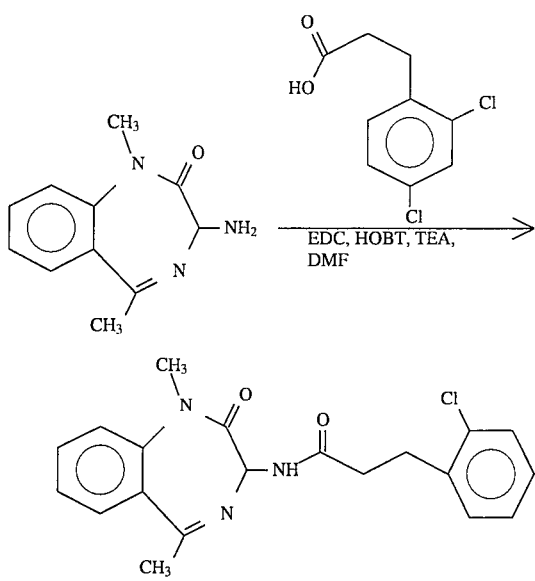

N-[2,3-dihydro-1-methyl-2-oxo-5-methyl-1H-1,4-benzodiazepin-3-yl]-3-(2,4-dichlorophenyl)propanamide was prepared in a similar manner as described previously.

m.p. 194°–195° C.

CHN: Anal. Calcd. for C,59.42; H, 4.74; N, 10.39 Observed: C,59.50; H, 4.74; N, 10.44

$^1$H NMR (CDCl$_3$) δ: 2.49 (brs, 3H), 2.65 (dt, 2H), 3.05 (t, 2H), 3.42 (s, 3H), 5.35 (d, 1H), 71–7.6 (m, 8H).

EXAMPLE 66

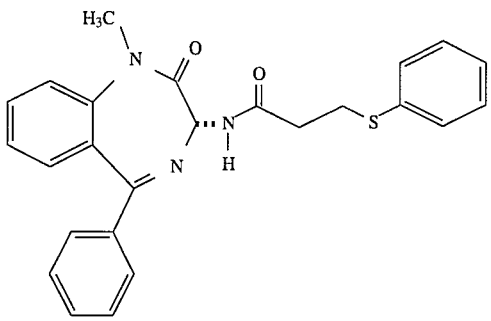

3R-(+)-3-(Phenylthio)-N-[2,3-dihydro-1-methyl-2-oxo-5-phenyl-1H-1,4-benzodiazepin-3-yl]-propanamide To a stirred solution of 3-Bromopropionic acid (1.0 g, 6.5 mmol) in DMF (20 mL) was added K$_2$CO$_3$ (1.8 g, 13 mmol) and thiophenol (0.72 g, 6.5 mmol). This was heated to 50° C. for 1 h. The rm was then diluted with 200 mL H$_2$O and extracted with 2×100 mL EtOAc. The combined organics were washed with 100 mL H$_2$O and dried with Na$_2$SO$_4$. This was evaporated to 1.52 g of a colorless oil, 1.18 g corrected for residual DMF by NMR.

The above oil was taken up in 30 mL DMF and 1-(3-Dimethylaminopropyl)-3-ethylcarbodiimide hydrochloride (2.45 g, 12.8 mmol) and 1-Hydroxybenztriazole hydrate (1.73 g, 12.8 mmol) were added. This was stirred for 5 min at rt. 3-(R)-Amino-1,3-dihydro-1-methyl-5-phenyl-2H-1,4-benzodiazepin-2-one (0.66 g, 2.6 mmol) was then added and the reaction was stirred at rt overnight. The reaction was diluted with 200mL H$_{20}$ and extracted with 2×150 mL EtOAc. The combined organics were washed with 1×100 mL H$_2$O, dried with Na$_2$SO$_4$ and evaporated. The residue was chromatographed over silica eluting with 2% MeOH:CHCl$_3$. Collected pure fractions, evaporated. Evaporated from diethyl ether to give 770 mg of a white foam.

Anal. Calcd for C$_{25}$H$_{23}$N$_3$O$_2$S.0.05Hexane: C, 70.04; H, 5.51; N, 9.69. Found: C 69.91, H 5.40, N 9.78.

EXAMPLE 67

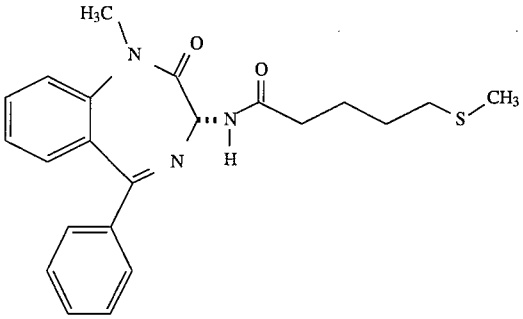

3R-(+)-5-(Methylthio)-N-[2,3-dihydro-1-methyl-2-oxo-5-phenyl-1H-1,4-benzodiazepin-3-yl]-propanamide To an aqueous solution of K$_2$CO$_3$ (0.76 g, 5.5 mmol) was added 5-Bromopentanoic acid and sodium thiomethoxide. This was stirred at rt overnight. The reaction was diluted with 50 mL H$_2$O and acidified to pH=0 with 6N HCl. Extracted with 2×50 mL EtOAc. Dried with Na$_2$SO$_4$, evaporated to 0.55 g of a yellow oil.

The above oil was taken up in 10 mL DMF and 1-(3-Dimethyl-aminopropyl)-3-ethylcarbodiimide hydrochloride (1.30 g, 6.8 mmol) and 1-Hydroxybenztriazole hydrate (0.92 g, 6.8 mmol) were added. 3-(R)-Amino-1,3-dihydro-1-methyl-5-phenyl-2H-1,4-benzodaizepin-2-one (0.85 g, 3.4 mmol) was then added and the reaction was stirred overnight at rt. The reaction was diluted with 100 mL H$_2$O and extracted with 2×50 mL EtOAc. Combined organics were dried with brine and Na$_2$SO$_4$, and evaporated to yellow oil. The residue was chromatographed over silica eluting with 50:50 EtOAc:Hex to 100% EtOAc. Pure fractions collected to give 1.33 g of a colorless oil. 0.4 g of which were chromatographed over silica eluting with 2% MeOH:CH$_2$Cl$_2$. Pure fractions were collected, evaporated. Evaporated from ethyl ether:hexane to give a white powder mp. 61°–65° C.

Anal. Calcd for C$_{22}$H$_{25}$N$_3$O$_2$S.0.35H$_2$O: C, 65.76; H, 6.45; N, 10.46. Found: C, 65.81; H, 6.21; N, 10.57.

EXAMPLE 68

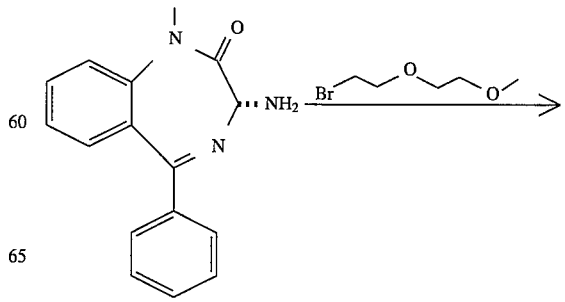

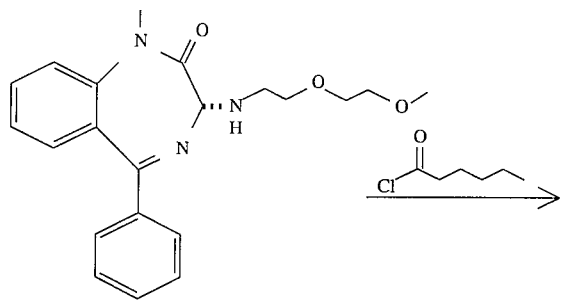

N-[2,3-dihydro-1-methyl-2-oxo-5-phenyl-1H-1,4-benzodiazepin-3-yl]-N-2-(2-methoxyethoxy)-ethylhexanamide 3-(R)-Amino-1,3-dihydro-1-methyl-5-phenyl-2H-1,4-benzodiazapin-2-one (1.33 g, 5.0 mmol) in N,N-dimethyl formamide (30 mL) was mixed with 1-bromo-2-(2-methoxyethoxy)-ethane (1.35 mL, 5.0 mmol) and triethylamine (1.0 mL). The mixture was stirred and heated at reflux for 4 h. After that time, the reaction was cooled to room temperature, diluted with 150 mL water, and extracted with ethyl acetate (3×100 mL). The organic layers were combined, dried with magnesium sulfate, gravity filtered, and the solvent was removed in vacuo. The resulting oil was chromatographed over silica in 1:1 ethyl acetate:hexane, yielding the mono-alkylated product (1.2 g, 65%) as well as the starting 1,4-benzodiazapin-2-one and bis-alkylated material. To a solution of the mono-alkylated material (1.2 g, 3.27 mmol) in methylene chloride (20 mL) was added hexanoyl chloride (0.96 mL, 3.27 mmol) and the reaction was stirred for 0.25 h. The reaction was then diluted with methylene chloride (150 mL) and saturated aqueous sodium hydrogen carbonate (150 mL) was added. The aqueous portion was extracted again with methylene chloride (2×100 mL) and the organics were combined, dried with magnesium sulfate, gravity filtered, and the solvent was removed in vacuo. The resulting oil was chromatographed over silica with 1:1 ethyl acetate:hexane, yielding an oil, giving 580 mg (38%) of the product. $[\alpha]_d 0.00°$; c=0.27; MeOH.

Anal. Calcd. for $C_{27}H_{35}N_3O_4 \cdot 0.80$ mol $H_2O$: C, 67.56; H, 7.69; N, 8.75. Found: C, 67.56; H, 7.39; N, 8.85%.

EXAMPLE 69

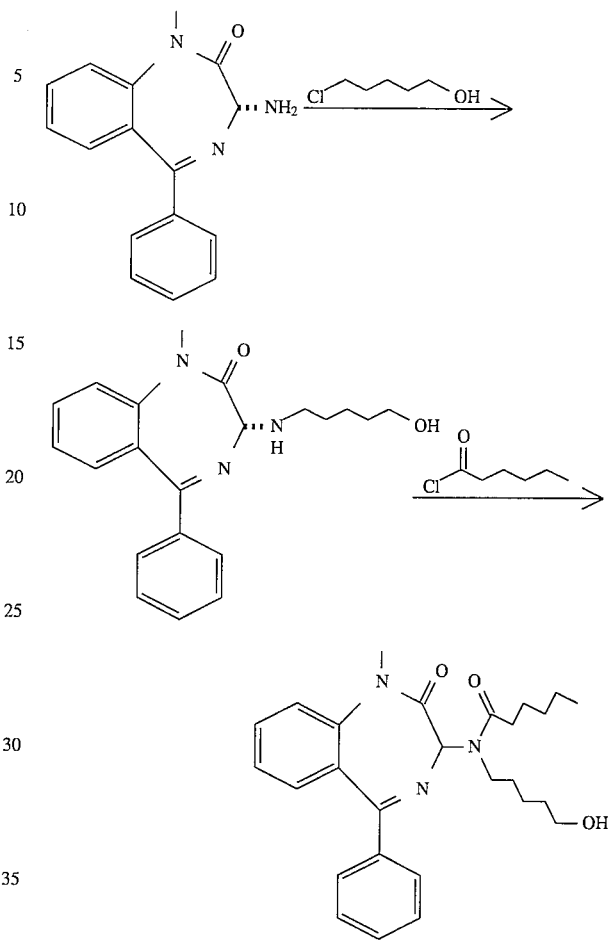

(+)-N-[2,3-dihydro-1-methyl-2-oxo-5-phenyl-1H-1,4-benzodiazepin-3-yl]-N-(5-hydroxypentyl)-hexanamide 3-(R)-Amino-1,3-dihydro-1-methyl-5-phenyl-2H-1,4-benzodiazapin-2-one (1.33 g, 5.0 mmol) in acetonitrile (40 mL) was mixed with 5-chloropentan-1-ol (0.61 g, 5.0 mmol) and sodium hydrogen carbonate (2.0 g) was suspended in the mixture. The mixture was stirred and heated at reflux for 12 h. After that time, the reaction was cooled to room temperature, diluted with 100 mL water, and extracted with ethyl acetate (3×75 mL). The organic layers were combined, dried with magnesium sulfate, gravity filtered, and the solvent was removed in vacuo. The resulting oil was chromatographed over silica in 1:49 methanol:chloroform yielding the mono-alkylated product (1.1 g, 62%) as well as the starting 1,4-benzodiazapin-2-one and bis-alkylated material. To a solution of the monoalkylated material (0.50 g, 1.42 mmol) in methylene chloride (30 mL) was added hexanoyl chloride (0.20 mL, 1.42 mmol) and the reaction was stirred for 0.25 h. The reaction was then diluted with methylene chloride (100 mL) and saturated aqueous sodium hydrogen carbonate (100 mL) was added. The aqueous portion was extracted again with methylene chloride (2×77 mL) and the organics were combined, dried with magnesium sulfate, gravity filtered, and the solvent was removed in vacuo. The resulting oil was chromatographed over silica with 1:1 ethyl acetate:hexane, yielding a foam, giving 360 mg (64%) of the product. foam, $[\alpha]_d$ (+)8.36° (c=0.61, MeOH).

Anal. Calcd. for $C_{27}H_{35}N_3O_2 \cdot 0.25$ mol $H_2O$: C, 71.42; H, 7.88; N, 9.25. Found: C, 71.47; H, 7.89; N, 9.12%.

EXAMPLE 70

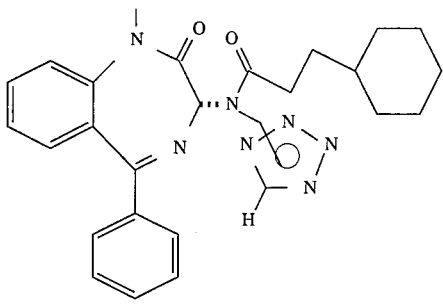

(+)-3-Cyclohexyl-N-[2,3-dihydro-1-methyl-2-oxo-5-phenyl-1H-1,4-benzodiazepin-3-yl]-N-(tetrazolylmethyl)propanamide (+)-N-[2,3-dihydro-1-methyl-2-oxo-5-phenyl-1H-1,4-benzodiazepin-3-yl]-N-(hydroxymethyl)hexanamide (0.67 g, 1.56 mmol) was dissolved in methylene chloride(100 mL), along with tetrazole (0.33 g, 4.7 mmol), and then, N,N-diisopropyl-dibenzyl-phosphoramidite (1.07 g, 3.1 mmol). After 2 h, the mixture was diluted with methylene chloride (150 mL), and extracted with saturated aqueous sodium hydrogen carbonate (3×100 mL). The organic layers were combined, dried with magnesium sulfate, gravity filtered, and the solvent was removed in vacuo. The resulting oil was chromatographed twice over silica with 1:1 ethyl acetate:hexane, yielding two constitutional isomers, a (65 mg, 9%) and b (56 mg, 7.5%).

Isomer A:
m.p. 96°–98° C., $[\alpha]_d$+188.9° (c=0.19, MeOH).
Anal. Calcd. for $C_{27}H_{31}N_7O_2 \cdot 0.30$ mol TFA: C, 63.78; H, 6.07; N, 18.86. Found: C, 63.7; H, 6.12; N, 18.76%.

Isomer B:
m.p. 92°–95° C., $[\alpha]_d$+81.3° (c=0.31, MeOH).
Anal. Calcd. for $C_{27}H_{31}N_7O_2 \cdot 0.35$ mol TFA: C, 63.31;H, 6.01; N, 18.66. Found: C, 63.35; H, 6.02; N, 18.74%.

What is claimed is:

1. A method of treating cardiac arrhythmia in mammals comprising block of the slowly activating delayed rectifier potassium (K+) current ($IK_s$) and the rapidly activating and deactivating delayed rectifier potassium current ($IK_r$), wherein the slowly activating delayed rectifier potassium ($K^+$) current ($IK_s$) in isolated myocytes is selectively blocked by a compound at a concentration of 1 μM or less ($IC_{50}$) and the concentration that blocks IKs by 50% is at least 10 fold lower than the concentration required to cause 50% block of $IK_r$ and or $IK_1$.

* * * * *